(12) United States Patent
Dabney et al.

(10) Patent No.: US 6,620,157 B1
(45) Date of Patent: Sep. 16, 2003

(54) HIGH FREQUENCY POWER SOURCE

(75) Inventors: James Huntington Dabney, Irvine, CA (US); Richard L. Quick, Mission Viejo, CA (US); Conrad Sawicz, Tustin, CA (US); Paul Lubock, Laguna Niguel, CA (US); Dan Kussman, Aliso Viejo, CA (US)

(73) Assignee: SenoRx, Inc., Aliso Viejo, CA (US)

( * ) Notice: Subject to any disclaimer, the term of this patent is extended or adjusted under 35 U.S.C. 154(b) by 0 days.

(21) Appl. No.: 09/752,978

(22) Filed: Dec. 28, 2000

(51) Int. Cl.[7] .............................................. A61B 18/18
(52) U.S. Cl. ........................... 606/34; 606/39; 606/40; 606/45; 606/49; 607/101
(58) Field of Search .......................... 606/32, 34, 35, 606/39, 40, 41, 42, 46–50; 607/96, 98, 99–101, 113, 115, 116, 119

(56) References Cited

U.S. PATENT DOCUMENTS

| | | |
|---|---|---|
| 4,517,976 A | 5/1985 | Murakoshi et al. |
| 4,658,819 A | 4/1987 | Harris et al. |
| 4,878,493 A | 11/1989 | Pasternak et al. |
| 5,772,659 A | 6/1998 | Becker et al. |
| 5,849,009 A | 12/1998 | Bernaz ........................ 606/36 |
| 5,976,128 A | 11/1999 | Schilling et al. |
| 5,997,535 A | 12/1999 | Betsill et al. ................. 606/43 |
| 6,022,347 A | 2/2000 | Lindenmeier et al. |
| 6,036,681 A | 3/2000 | Hooven |
| 6,066,134 A | 5/2000 | Eggers et al. |
| 6,391,024 B1 * | 5/2002 | Sun et al. ..................... 606/34 |

FOREIGN PATENT DOCUMENTS

EP 1 051 948 A 11/2000

OTHER PUBLICATIONS

*Force FX™ Electrosurgical Generator Instant Response To Tissue Density*, Instant Response Technology, http://www.valleylab.com/PRODUCTS/fx.htm, Electrosurgical Generators pp. 1–4.
*NEW! Force EZ™ Electrosurgical Generator Instant Response To Tissue Density*, Instant Response Technology, http://www.valleylab.com/PRODUCTS/fx.htm, Electrosurgical Generators pp. 1–4.
*Amplifiermodule 1–30MHz 150 Watts*, LCF Enterprises RF Power Amplifiers, www.lcfamps.com, pp. 1–2.
International Search Report, PCT/US01/49207, mailed Jun. 6, 2002.

* cited by examiner

Primary Examiner—Rosiland S. Kearney
(74) Attorney, Agent, or Firm—Duane Morris LLP

(57) ABSTRACT

A high frequency electrosurgical power generator configured to produce electrical power at a frequency of about 1 to about 14 MHz and preferably having an essentially sinusoidal waveform with a voltage level up to 1,000 Vrms, and a current level up to 5 Amps. The output of the high frequency electrosurgical power generator is connected to an electrosurgical tool configured to receive the voltage and current produced by the electrosurgical power generator and deliver the voltage and current to an electrosurgical site. The output of the electrosurgical generator preferably is an essentially sinusoid waveform with a frequency between about 3 MHz and about 8 MHz, up to about 700 volts rms, up to about 2 amps, with a total power of up to 1,000 watts.

20 Claims, 36 Drawing Sheets

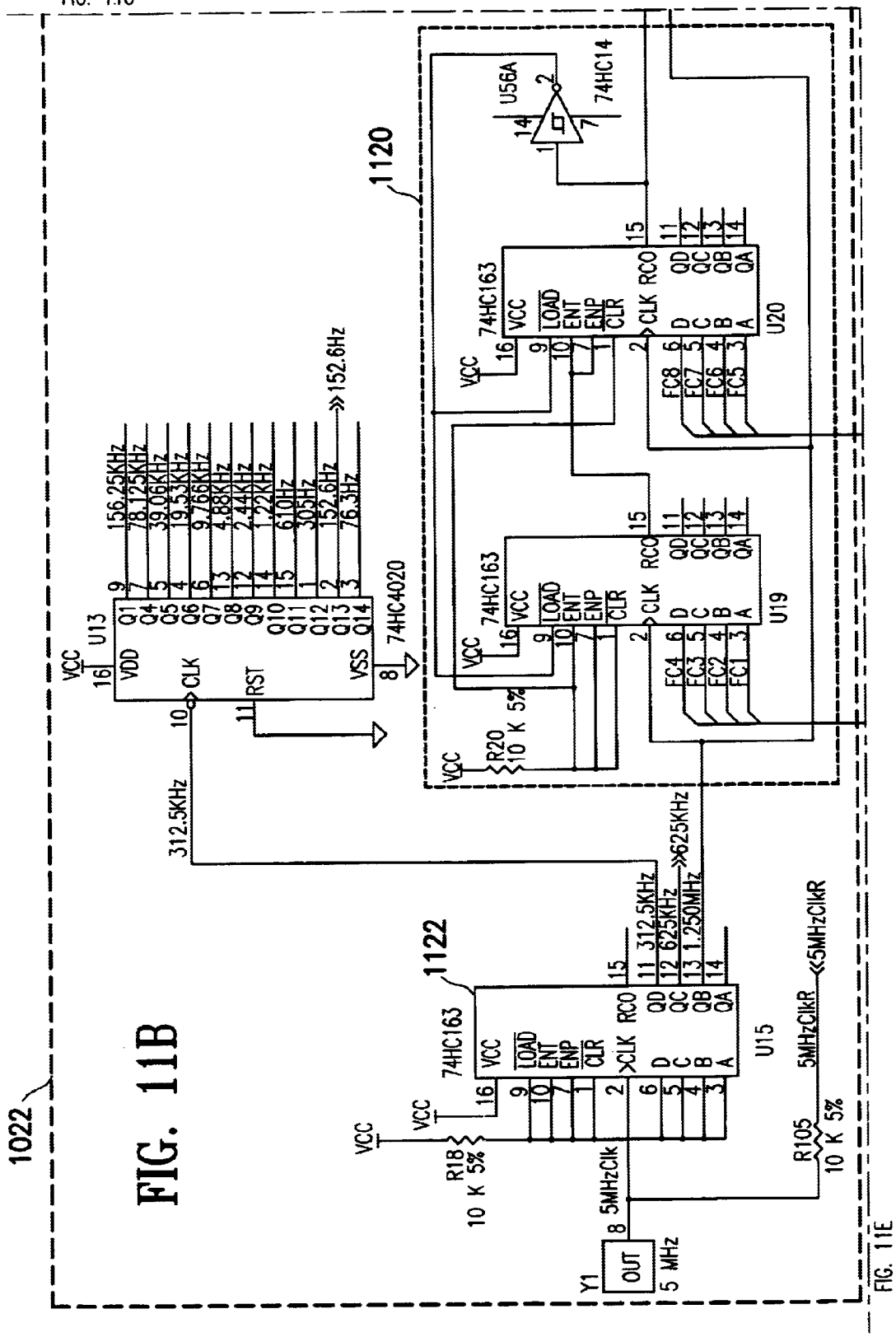

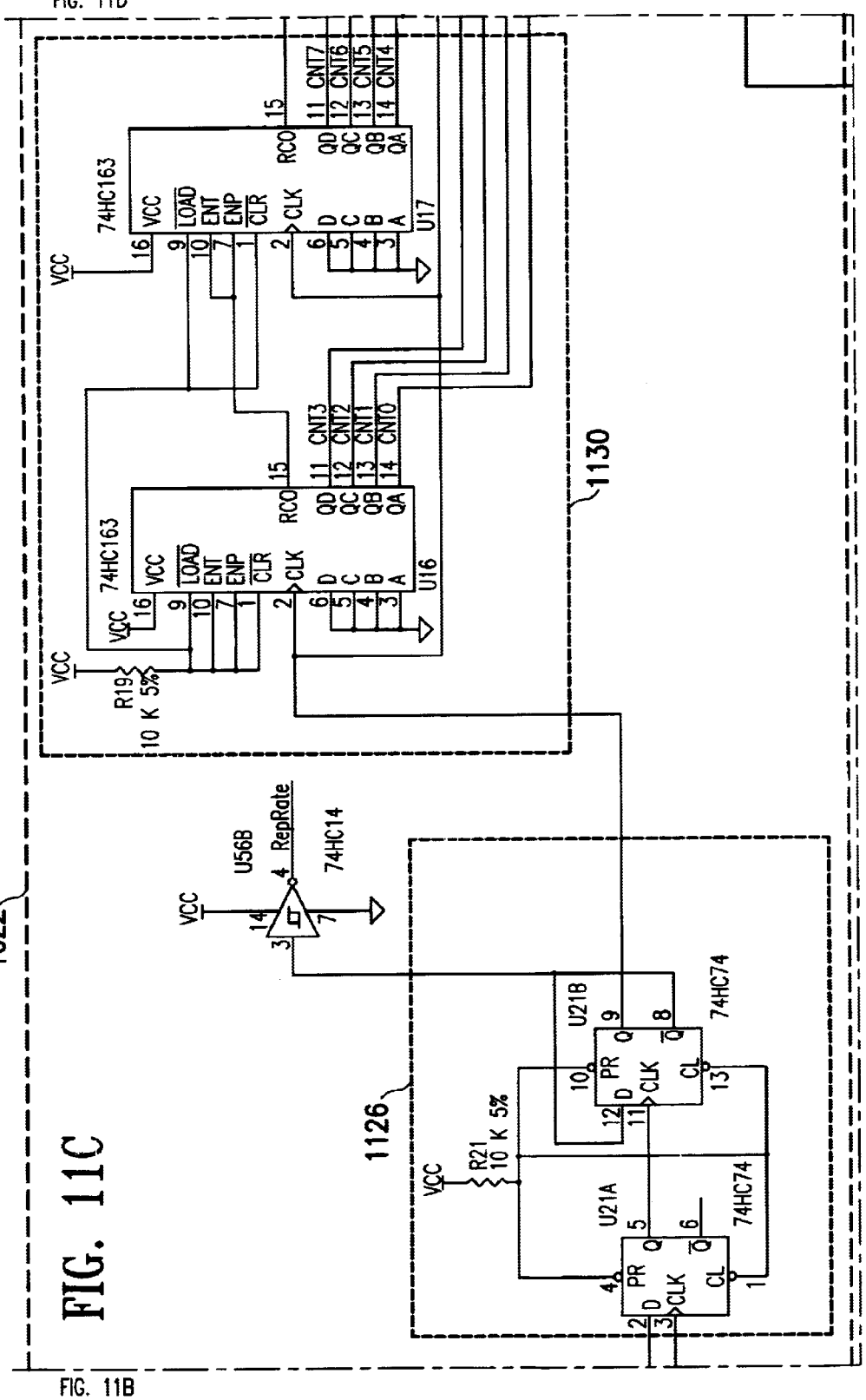

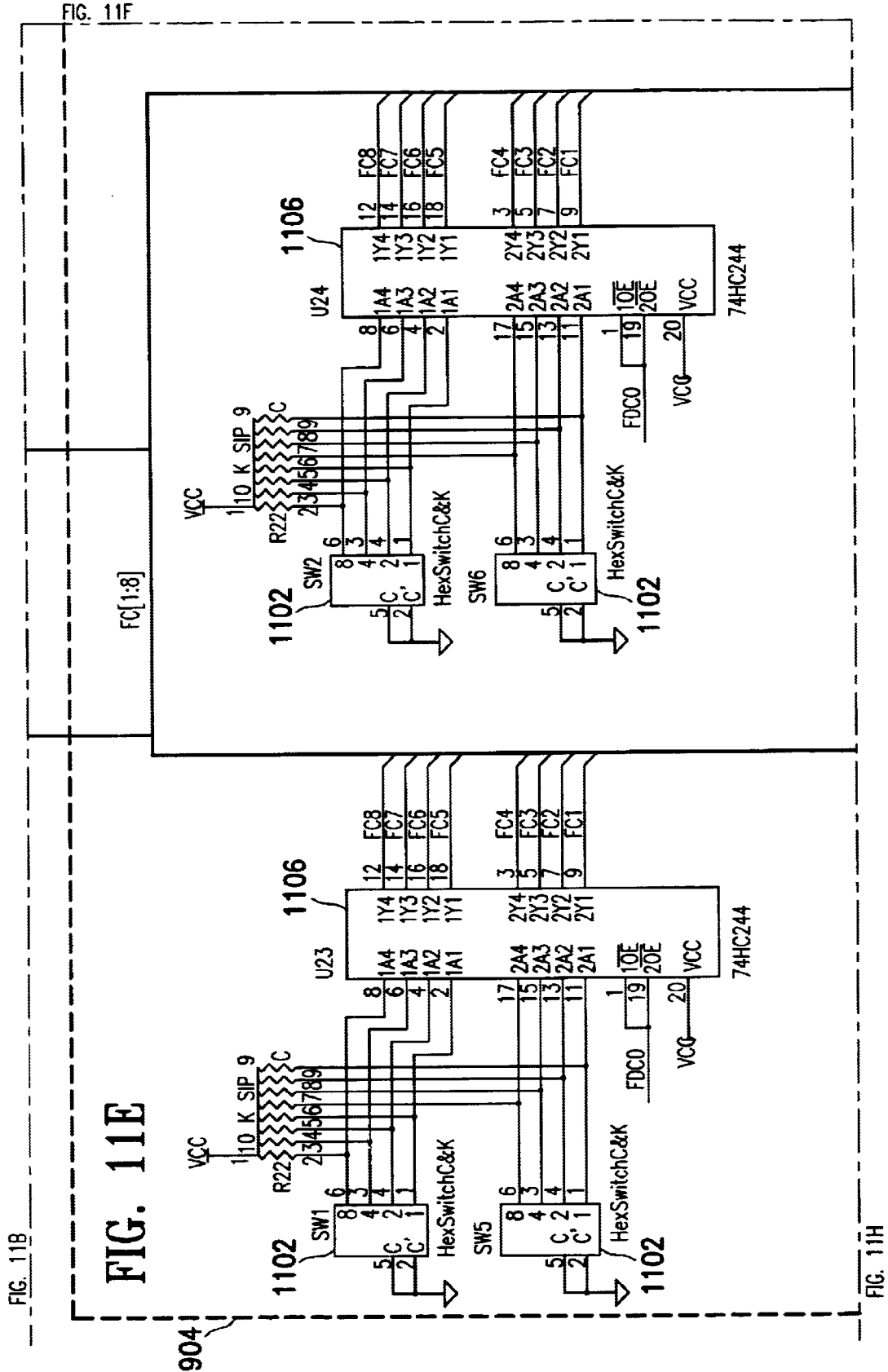

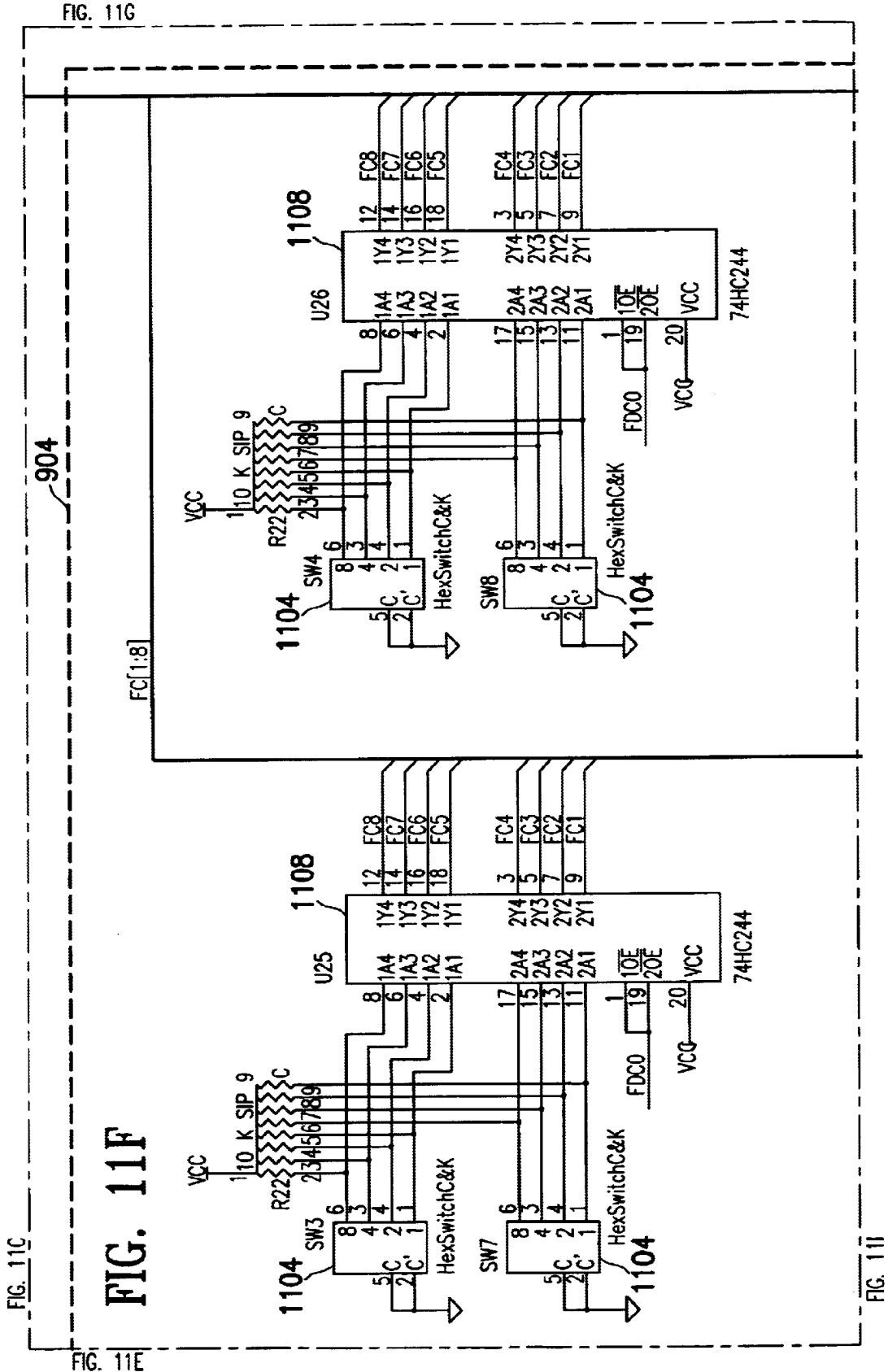

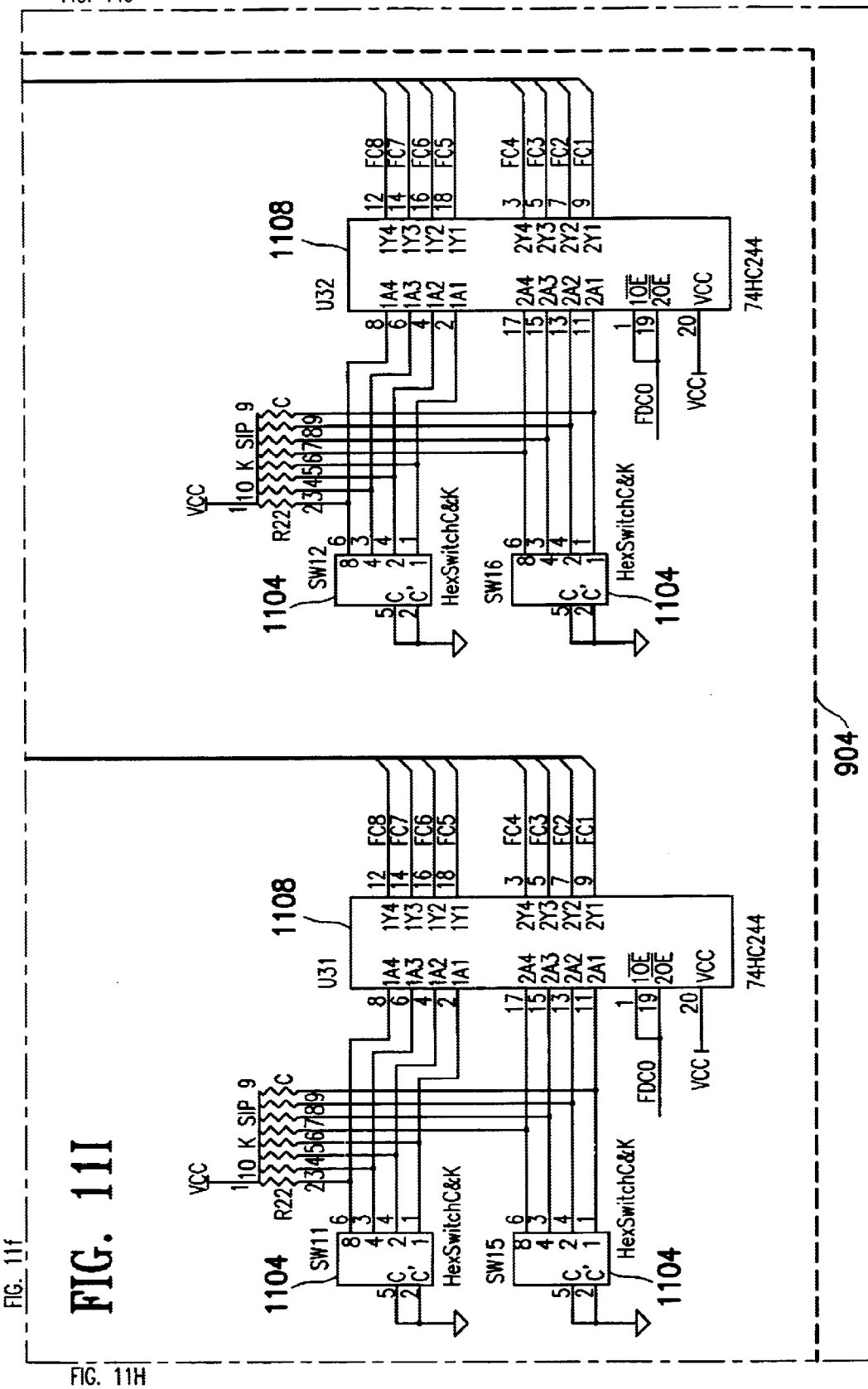

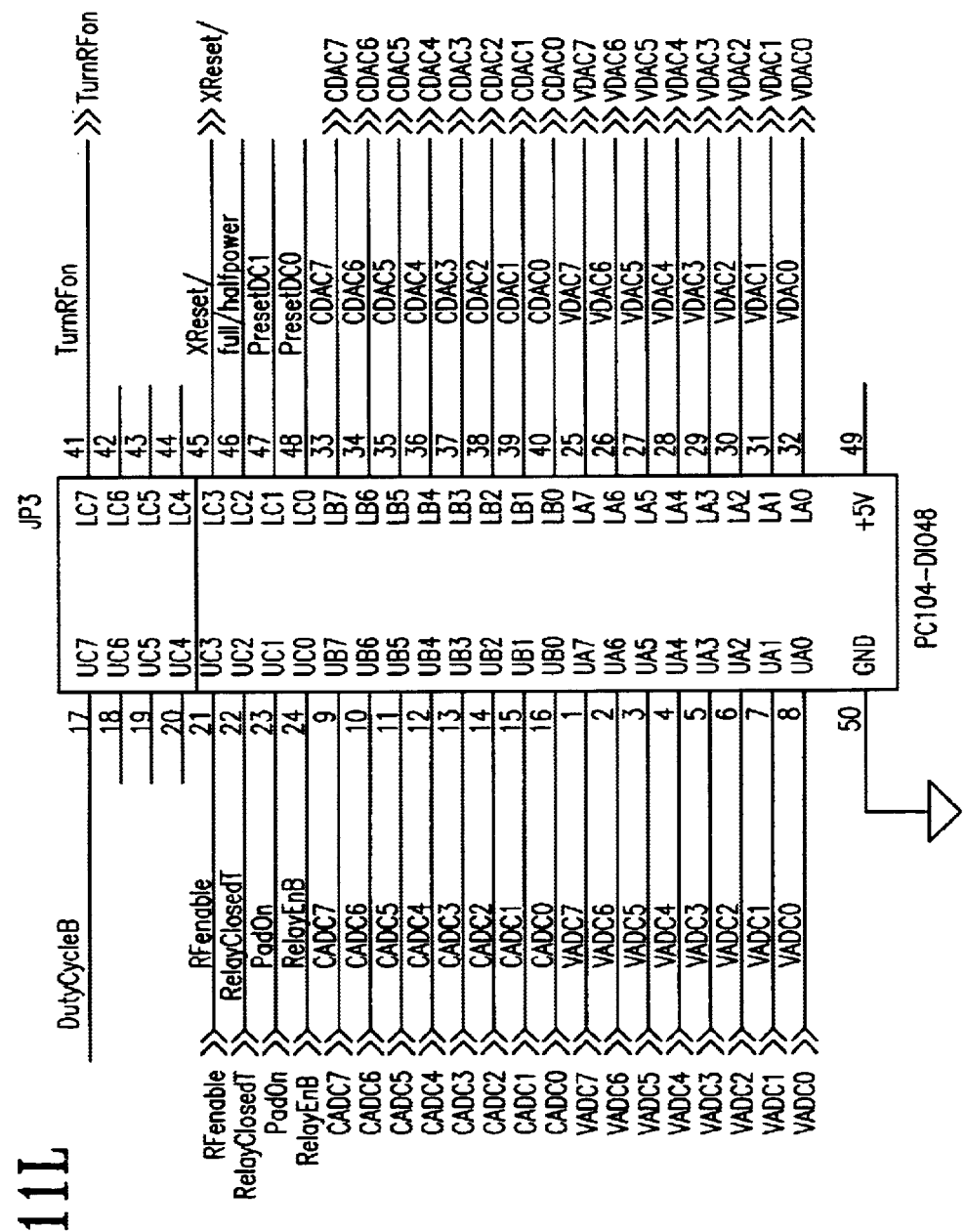

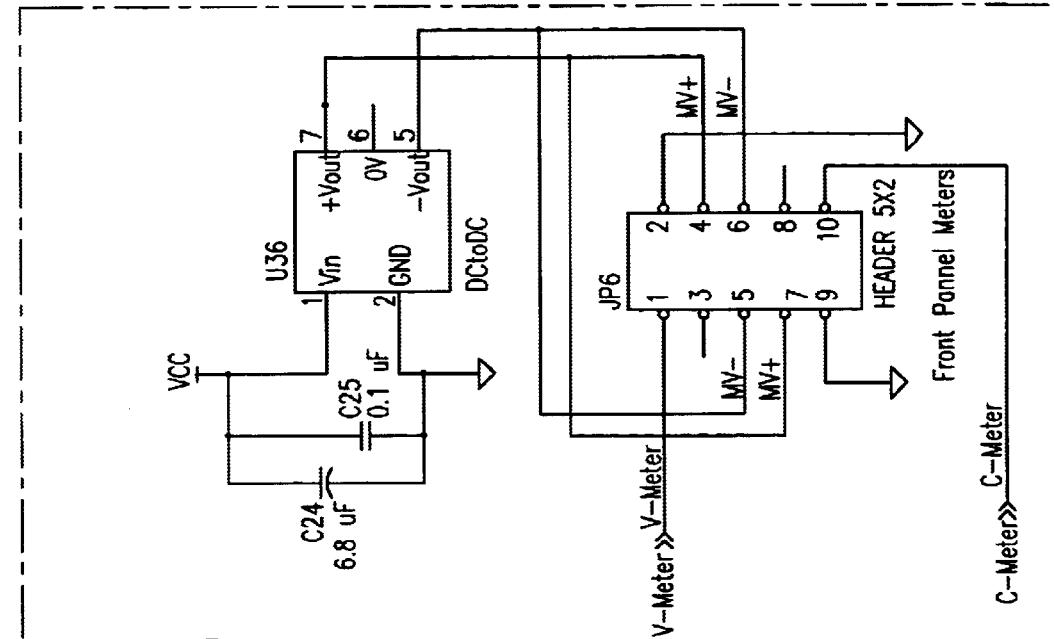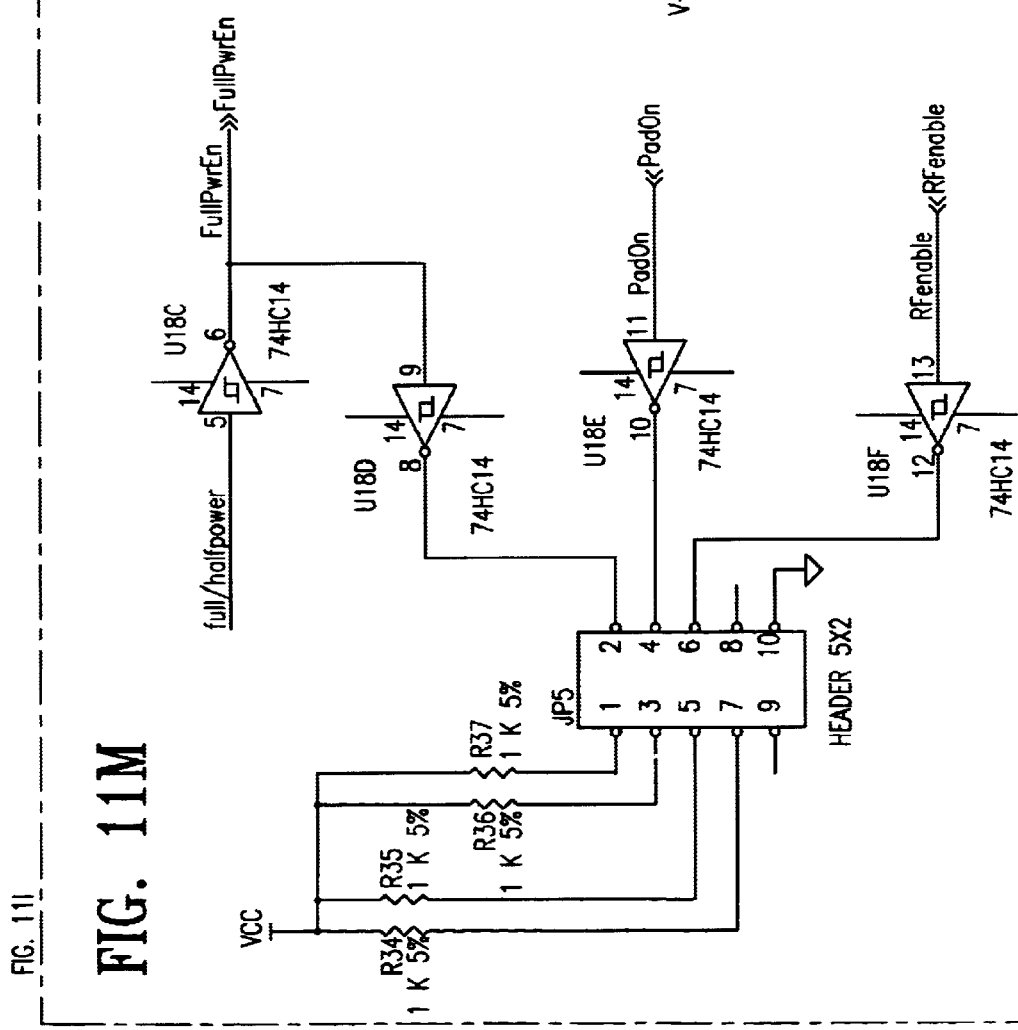

FIG. 12E

HIGH FREQUENCY POWER SOURCE

BACKGROUND OF THE INVENTION

Power generators used in electrosurgical procedures deliver electrical energy to an electrosurgical tool for operating on the tissue of a patient. An active electrode of the tool, connected to the power generator, concentrates the delivery of the electrical energy to a relatively small region of tissue of the patient. The electrical energy typically includes energy in the radio frequency (RF) band. The concentration of electrical energy facilitates cutting or coagulation of the tissue of the patient. During typical operation of a monopolar electrosurgical device, an alternating electrical current from the generator flows from an active electrode to a return electrode by passing through the tissue and bodily fluids of a patient.

During an electrosurgical operation, different tissue types may be encountered, such as, for example, fat, connective, glandular and vascular tissues. Connective, glandular and vascular tissues can have similar characteristics in the way they react to electrical energy, specifically, they have similar characteristics of electrical impedance. Fat however, has significantly different electrical response characteristics. In particular, fat presents a higher impedance to the flow of electrical current than do the other types of tissues. The tissue of certain anatomical portions, or regions, of a patient's body may be largely heterogeneous on a macroscopic scale, such as on a scale commensurate with that of an electrosurgical cutting tool. For example, breast tissue has this heterogeneous property and can be made up of all the tissue types discussed above, i.e., fatty, glandular, connective and vascular tissues. The variations in electrical impedance exhibited by these various tissue types can be problematic when attempting to perform electrosurgical cutting in such heterogeneous, or non-homogeneous, tissue.

In a typical electrosurgical procedure, the amount of electrical energy delivered by a power generator must be carefully controlled. If insufficient power is delivered by the power generator, the tissue cutting of the electrosurgical procedure will be inhibited. If more power than necessary is delivered by the power generator there may excessive, and unnecessary, collateral tissue damage making it more difficult to perform a histology on a sample and thereby decreasing the ability of a pathologist to diagnosis the sample, as well as resulting in a more difficult recovery by the patient in addition to other sequela. Using a regulated power generator helps control and stabilize the electrical energy delivered into the patient's tissue. However, due to the different electrical response characteristics of the various tissue types that may be present, the energy coupled into the tissue may vary even if the power generator is regulated. Generally, typical RF power generators experience difficulty in cutting through fatty non-homogeneous tissue because of the non-homogeneous tissue types that are typically encountered.

In addition, typical RF power generators are only effective with tools having small cutting surfaces. Thus, during an electrosurgical procedure, if fat is encountered, a surgeon must perform surgical cuts by "feathering", making repetitive shallow cuts with countertraction over the same area to attain a desired depth of cut. In addition, because typical power generators are only effective for tools with small cutting surfaces, the types of tools available to a surgeon during electrosurgery are limited.

There is a need in the art for improved electrosurgical RF power generators that can be used with electrosurgical tools that encounter non-homogeneous tissue, such as, for example, breast biopsy instruments. Electrosurgical tools, such as electrosurgical breast biopsy instruments, can present varying load requirements to an electrosurgical power generator than typical electrosurgical tools, due to the heterogeneous nature of the tissue they are used to cut or coagulate.

From the discussion above, it should be apparent that there is a need for an electrosurgical power generator used in electrosurgical procedures that will more effectively couple electrical energy to different types of tissue, in particular heterogeneous tissue that includes fat tissue. In addition, there is a need for a power generator that works effectively with large cutting surfaces, thereby expanding the types of tools that are available for electrosurgery.

The present invention satisfies these and other needs.

SUMMARY OF THE INVENTION

The invention is directed to a high frequency electrical power generator particularly suitable for use in electrosurgery.

An electrical power generator constructed in accordance with the invention is configured to produce electrical power at a frequency of about 1 MHz to about 14 MHz, preferably about 3 MHz to about 8 MHz. The electrical power generated preferably has an essentially sinusoidal waveform with a total harmonic distortion (THD) of less than 5%. The specified frequency and waveform help to minimize damage to adjacent tissue during electrosurgery. The power output has a high voltage level, for example, up to about 1,000 Vrms, and a high current level for example, between about 0.5 amps to 5 amps, particularly about 1 amp to 2 amps. The output of the electrosurgical power generator is connected to an electrosurgical tool configured to receive the voltage and current produced by the electrosurgical power generator and deliver the voltage and current to an electrosurgical site on a patient. There is preferably at least one ground pad in electrical contact with the patient to complete an electrical circuit for the system comprising the generator and the tool, thereby providing a controlled return path for the current from the electrosurgical site to the electrosurgical power generator.

The system may also include a distal interface pod, located proximate to the electrosurgical site, connected to the output of the high frequency electrosurgical generator. In one embodiment, the distal interface pod is configured to present a desired load to the electrosurgical power generator. In addition, the distal interface pod may include safety and patient interface functions, as well as telemetry functions such as monitoring various parameters important to safety as well as control parameters, for example, the voltage and current produced by the electrosurgical power generator and delivered to the electrosurgical tool.

The high frequency characteristics described above improve the electrosurgical power generator's ability to deliver consistent power over a range of electrical impedance loads caused by variations in tissue types.

The high voltage characteristics described above facilitate the use of long electrodes during an electrosurgical procedure. Use of long electrodes may require substantially higher starting and sustaining voltages, particularly when fatty tissue is present, in contrast to when other types of tissue are encountered.

Electrical power output with an essentially sinusoidal waveform in an electrosurgical procedure concentrates the electrical power into cutting tissue, thereby reducing the total power required during the electrosurgical procedure. Reduction in total power results in less heating, and thereby less damage to collateral tissue. Total power delivered during an electrosurgical procedure may also be reduced through duty factoring where the power is turned "on" and then "off" in rapid succession. When duty factoring the power output, the waveshape envelope may be, for example, a ramped, or trapezoidal rectangle, or a zero crossing switched rectangle.

These and other features of the invention will become more apparent from the following detailed description of the invention and the accompanying exemplary drawings.

DETAILED DESCRIPTION OF THE INVENTION

Figure 1:
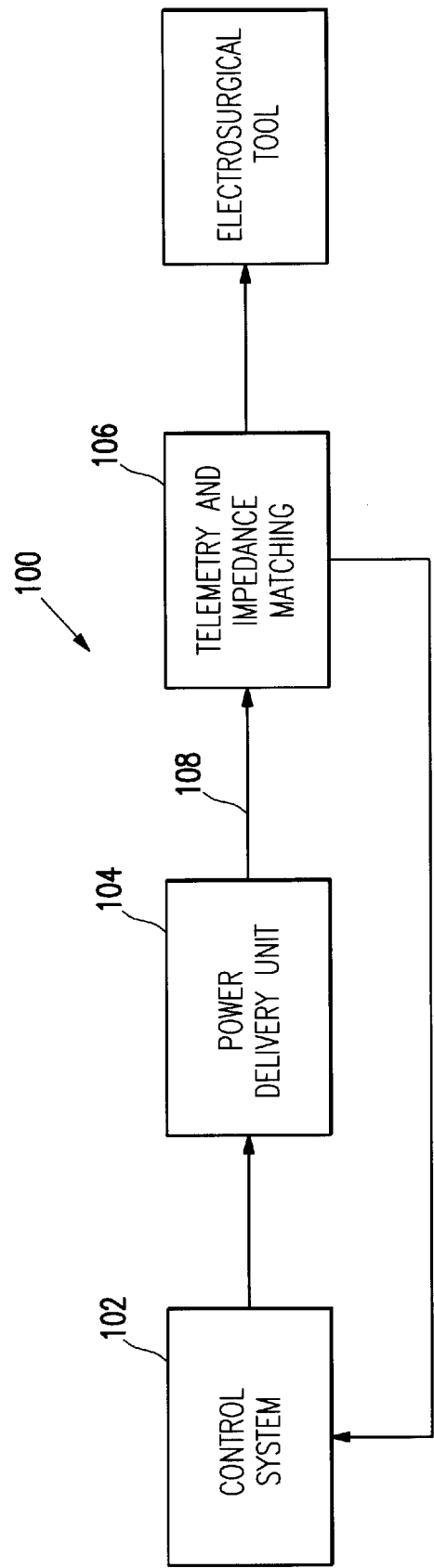
FIG. 1 is a block diagram illustrating a power delivery system constructed in accordance with the invention for use in an electrosurgical procedure.

FIG. 1 is a block diagram illustrating a power delivery system 100 constructed in accordance with the invention for use in an electrosurgical procedure. The power delivery system 100 includes a control system 102. The control system generates a desired waveform for use in the electrosurgical procedure. The control system 102 outputs the desired waveform to a power delivery unit 104. The control system 102 condition the waveform, including, for example, amplitude control, gating and duty actor control. Gating and duty factor control are explained in more detail below. The power delivery unit 104 receives the desired waveform, amplifies and provides electrical capability, and outputs a power waveform. In one embodiment the power delivery unit may be a voltage controlled electrical power generating unit configured to produce a high frequency current having an essentially sinusoidal waveform having a total harmonic distortion (THD) of less than 5%.

The power waveform output by the power delivery unit 104 is routed to a telemetry and impedance matching unit 106 via a cable 108. The telemetry and impedance matching unit 106 receives the power waveform. The telemetry and impedance matching unit 106 also provides an interface that efficiently transfers the power waveform to the electrosurgical tool. In addition, the telemetry and impedance matching unit 106 measures parameters of the power waveform and communicates these measurements back to the control system 102.

In one embodiment, the parameters measured by the telemetry and impedance matching unit 106 include the voltage and current of the power waveform delivered to the electrosurgical tool. In another embodiment, there is no telemetry and impedance matching unit 106. In this embodiment, the power waveform output by the power delivery unit 104 is connected directly to the electrosurgical tool.

Figure 2:
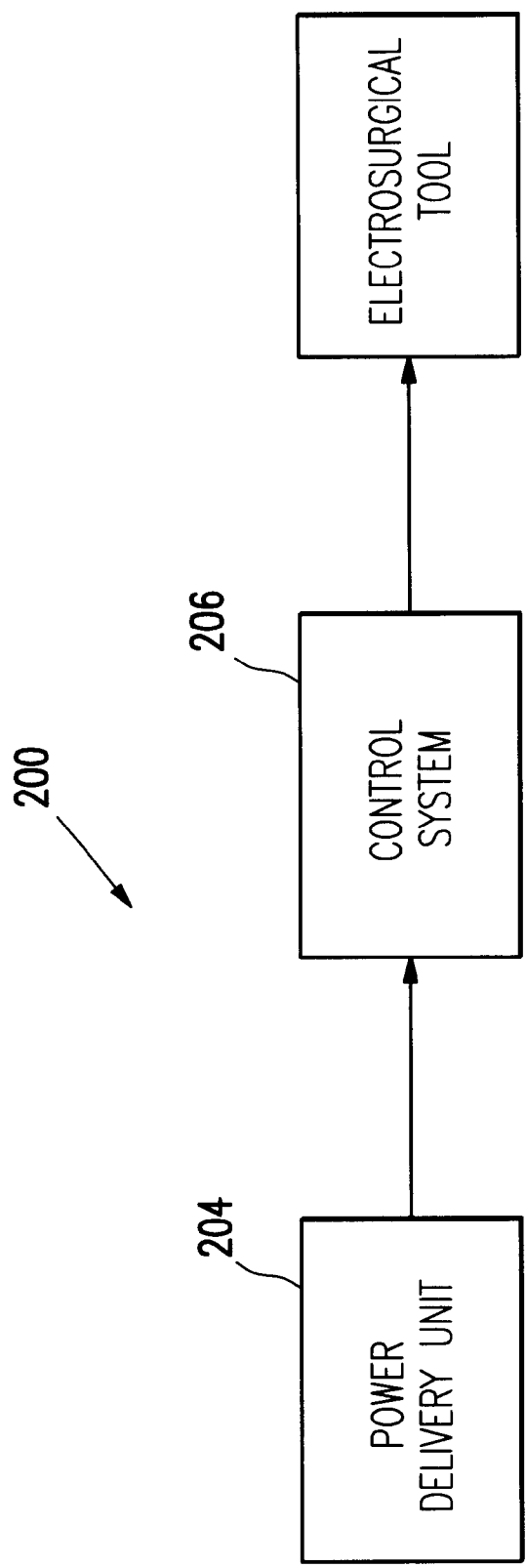
FIG. 2 is a block diagram illustrating another embodiment of a power delivery system constructed in accordance with the invention for use in an electrosurgical procedure.

FIG. 2 is a block diagram illustrating another embodiment of a power delivery system constructed in accordance with the invention for use in an electrosurgical procedure. In this embodiment, the power delivery system 200 includes a power delivery unit 204 configured to output a constant, high power output waveform. The high power waveform is routed to a control system 206. In this embodiment, the control system 206 is configured to receive the high power output waveform, condition the waveform and output a controller power waveform to the electrosurgical tool. The conditioning of the waveform may include, for example, amplitude control, gating, and duty factor control. Gating and duty factor control are explained in more detail below. In another embodiment, there may be an optional telemetry and impedance matching unit, as shown in FIG. 1, located between the control system and the electrosurgical tool. This embodiment may also include measurement of waveform parameters sent back to the control unit to be used to improve the power delivered to the electrosurgical tool.

Figure 3:
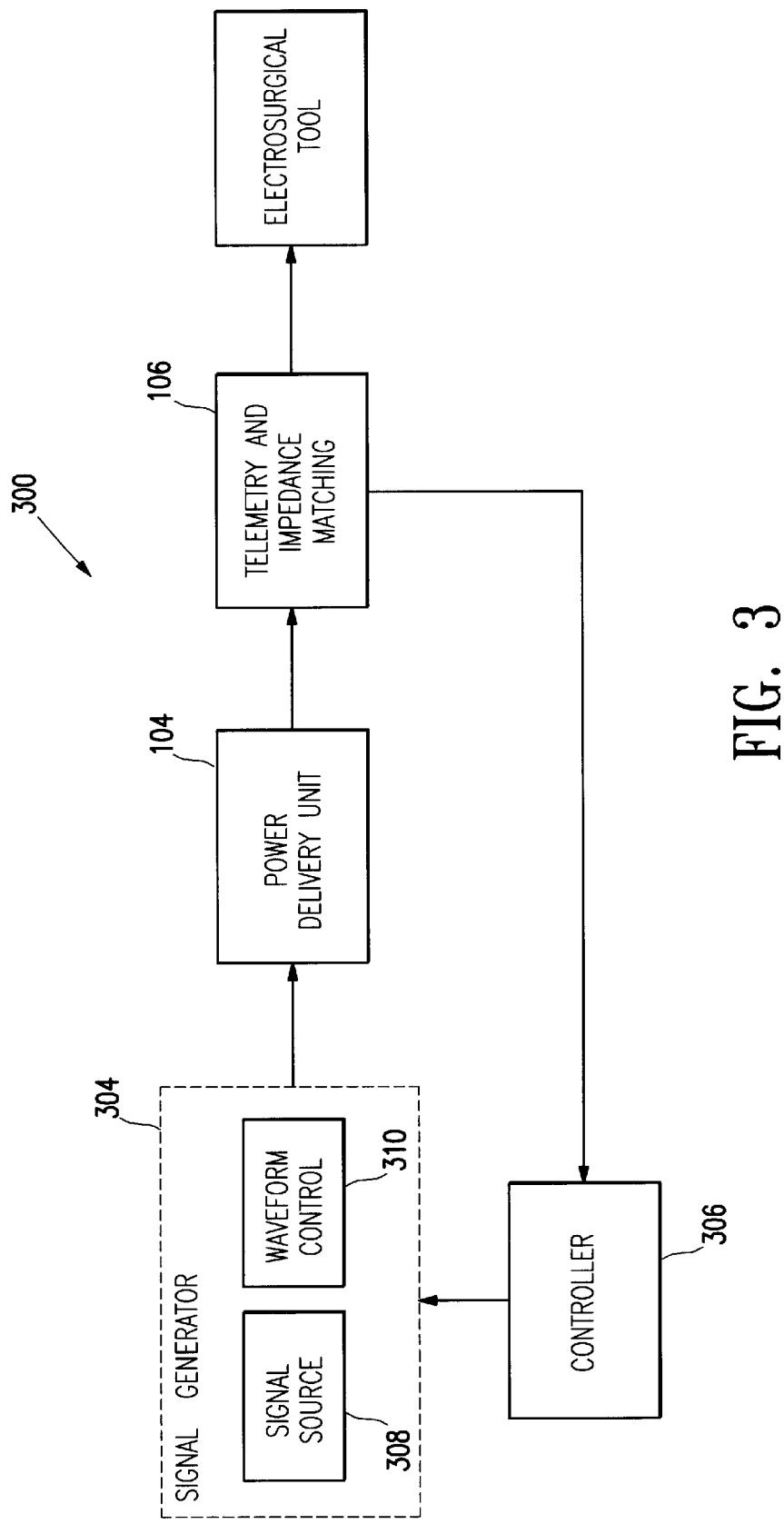
FIG. 3 is a block diagram illustrating yet another embodiment of a power delivery system constructed in accordance with the invention for use in an electrosurgical procedure.

FIG. 3 is a block diagram illustrating yet another embodiment of a power delivery system constructed in accordance with the invention for use in an electrosurgical procedure. In this embodiment, the power delivery system 300 includes a power delivery unit 104 and a telemetry and impedance matching unit 106 as described in relation to FIG. 1. The FIG. 3 embodiment includes a separate signal generator 304 and controller 306. The signal generator 304 includes a signal source 308 configured to output a continuous signal at a desired frequency. The signal source 308 output is routed to a waveform control unit 310. The waveform control unit 310 receives the signal source 308 output and conditions it to produce a desired signal to be sent to the power delivery unit 104. The conditioning may include, for example, gating and duty factor control. The controller 306 receives measurement data of waveform parameters delivered to the electrosurgical tool from the telemetry and impedance matching unit 106. The controller 306 adjust the operation of the signal source 308 and the waveform control unit 310 to deliver the desired waveform to the electrosurgical tool as measured by the telemetry and impedance matching unit 106.

Figure 4:
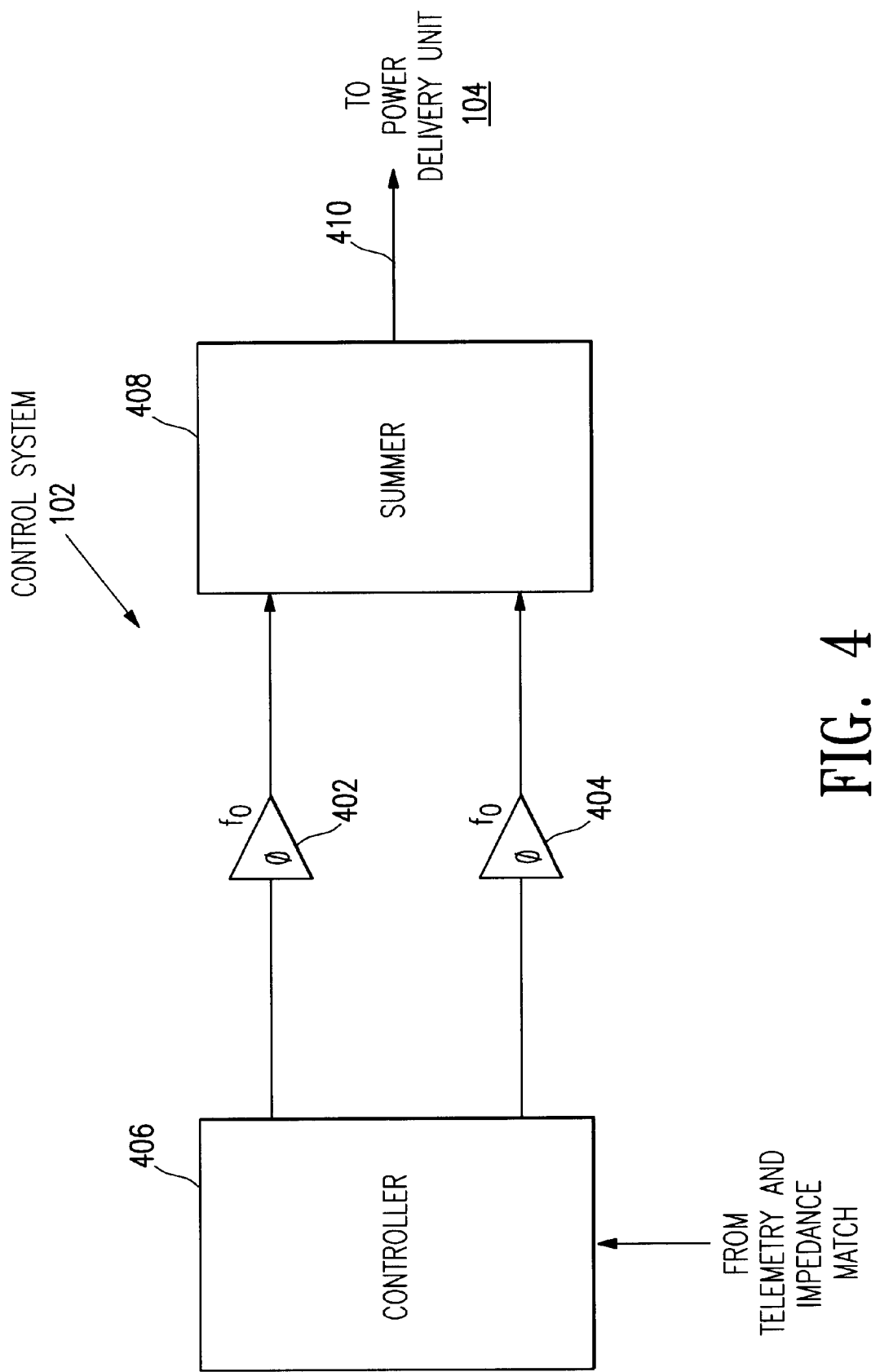
FIG. 4 is a block diagram of one embodiment of a control system for use in a power delivery system constructed in accordance with the invention.

FIG. 4 is a block diagram of one embodiment of the control system 102 for use in a power delivery system constructed in accordance with the invention. In this embodiment, the control system 102 includes a first signal source 402 and a second signal source 404. The two signal sources generate sinusoidal signals at a desired frequency $f_o$. The output of the two signal sources are combined in a summer 408. The summer 408 combines the outputs of the two signal sources 402 and 404 and outputs a combined signal 410 to the power delivery unit 108. A controller 406 receives measurements from the telemetry and impedance matching unit (not shown in FIG. 4) that relate to the power delivered to the electrosurgical tool. In response to the measurement signals received the controller 406 adjusts the phase relationship between the two signal sources 402 and 406. By adjusting the phase relationship between the two signal sources 402 and 404, a desired combined signal 410 is output by the summer 408 to the power delivery unit(not shown in FIG. 4).

Figure 5:
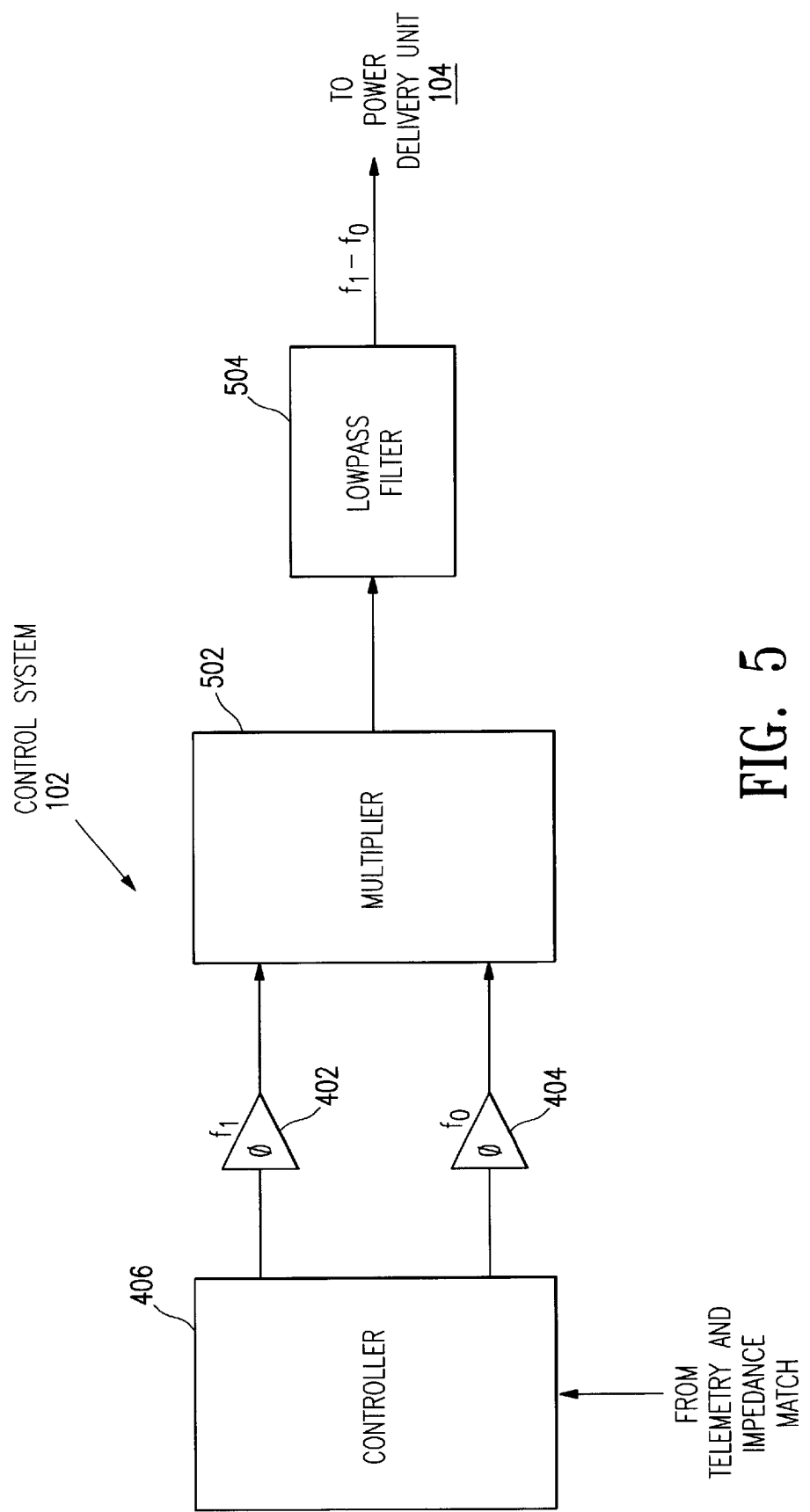
FIG. 5 is a block diagram of another embodiment of a control system for use in a power delivery system constructed in accordance with the invention.

FIG. 5 is a block diagram of another embodiment of a control system for use in a power delivery system. In this embodiment, the control system 102, as discussed in FIG. 4, includes a first signal source 402, a second signal source 404, and a controller 406. In this embodiment, the first signal source 402 and the second signal source 404 operate at different frequencies $f_1$ and $f_o$ respectively. The output of the two signal sources are routed to a multiplier 502, where the two signals are multiplied together. The output of the multiplier 502 contains, among other components, the difference between the two frequencies. The output of the multiplier 502 is routed to a lowpass filter 504. The lowpass filter attenuates components in the output waveform of the multiplier 502 except the component of the waveform at the difference frequency between the two signal sources. The output of the lowpass filter 504 is a waveform with a desired frequency of $f_1-f_o$. The output of the lowpass filter 504 is routed to the power delivery unit (not shown in FIG. 5).

Figure 6:
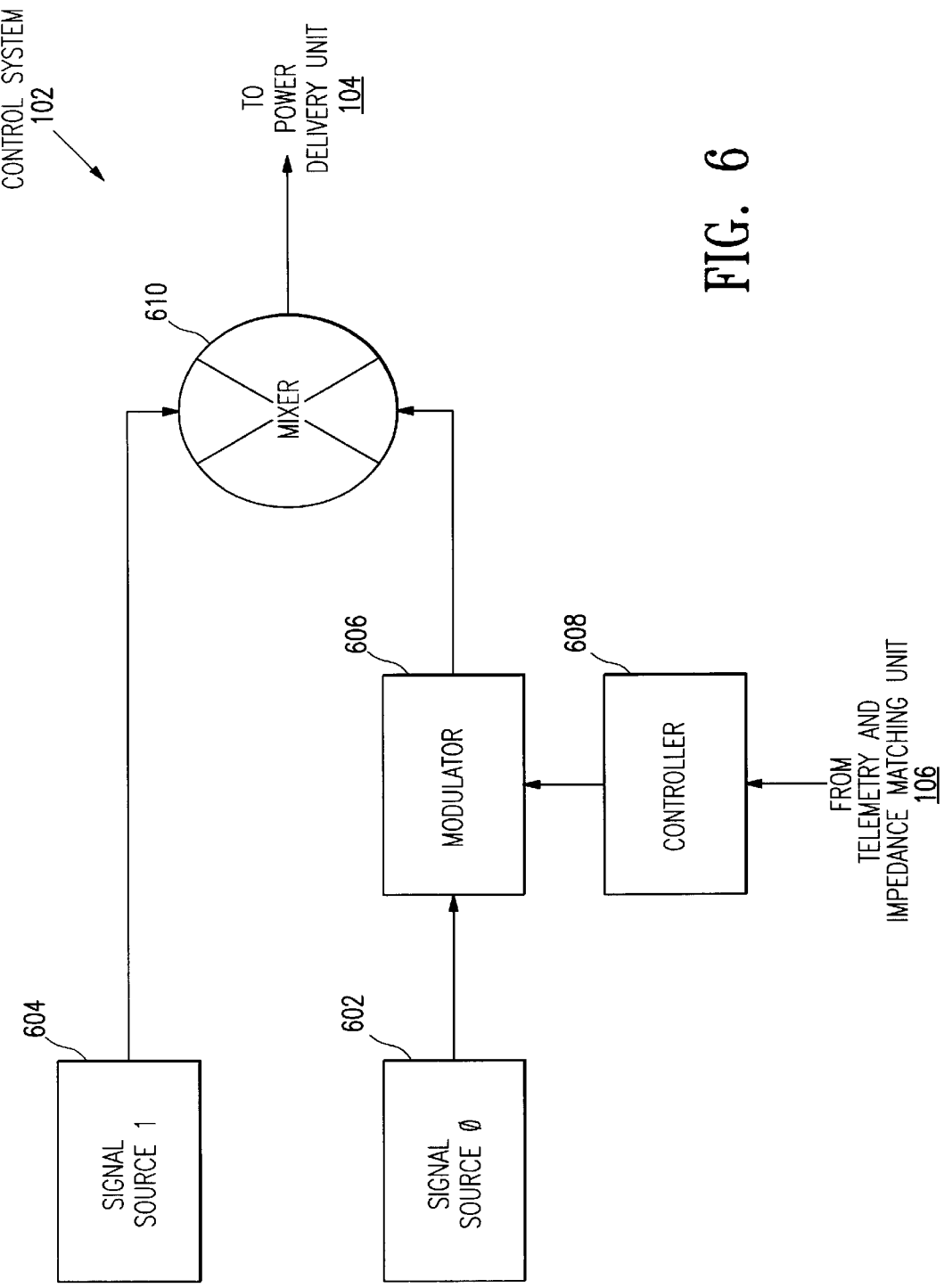
FIG. 6 is a block diagram of another embodiment of a control system for use in a power delivery system constructed in accordance with the invention.

FIG. 6 is a block diagram of another embodiment of a control system for use in a power delivery system in accordance with the invention. In this embodiment, there is a first signal source 602 and a second signal source 604. The output of the first signal source 602 is routed to a modulator 606. The modulator may adjust the phase, amplitude, or the phase and the amplitude of the signal received from the first signal source. The adjustments made by the modulator 606 are determined by a controller 608. For example, the controller 608 may receive telemetry and impedance matching data from the telemetry and impedance matching unit 106 and determine a desired modulation in response to the received data. The adjusted signal from the modulator 608 is routed to mixer 610. The other input to the mixer 610 is the output from the second signal source 604. For example, the mixer 610 may sum the two waveforms. The mixer 610 combines the two waveforms and outputs a combined waveform to the power delivery unit 104.

Figure 7:
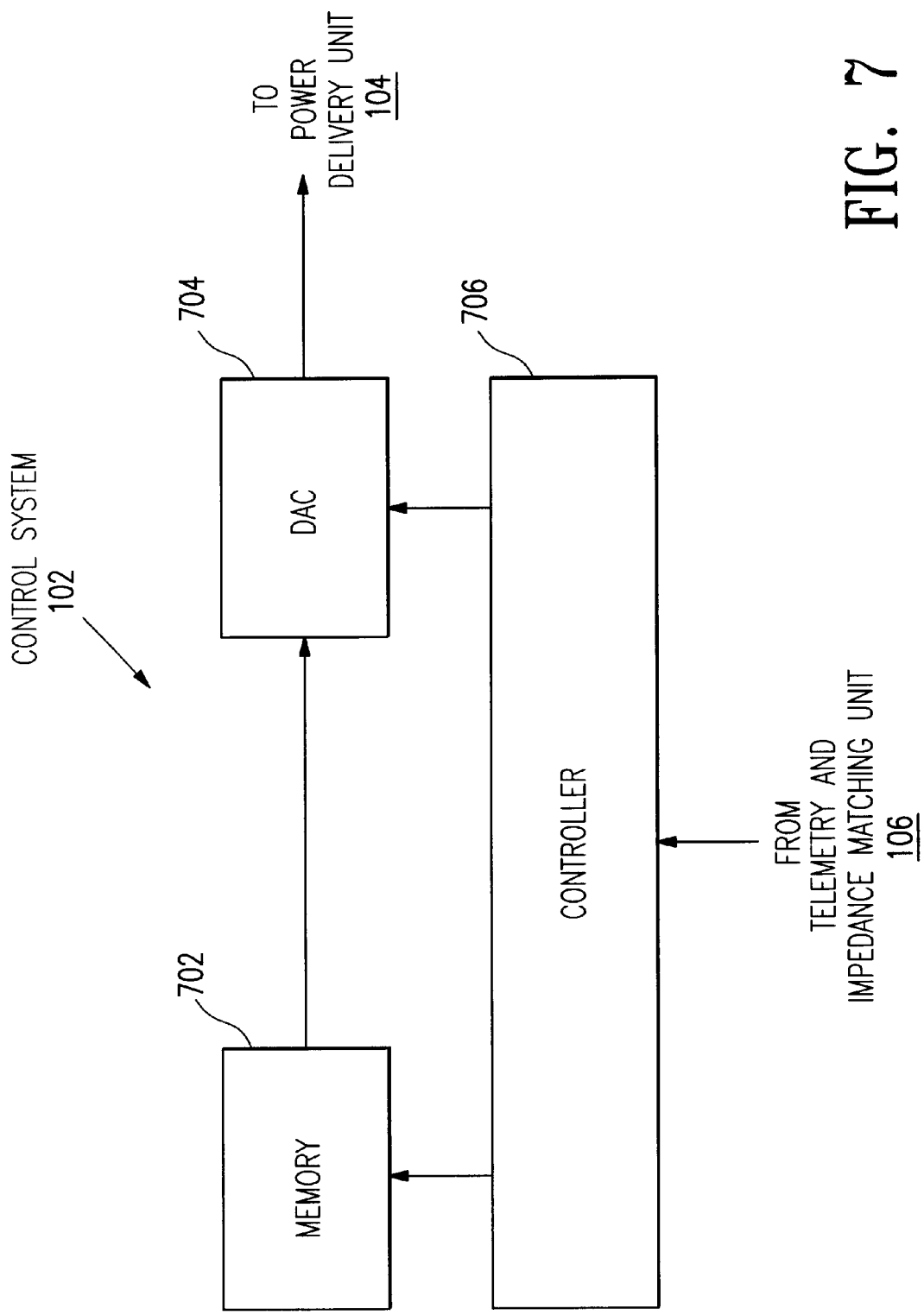
FIG. 7 is a block diagram of yet another embodiment of a control system for use in a power delivery system constructed in accordance with the invention.

FIG. 7 is a block diagram of yet another embodiment of control system for use in a power delivery system in accordance with the invention. In the embodiment, the control system 102 includes a memory 702 configured to store data to be used in generating a desired waveform. The memory 702 is in communication with a digital to analog converter (DAC) 704 and a controller 706. The controller 706 is also in communication with the DAC 704. A desired set of data stored in memory 702 corresponding to a desired waveform is transferred from the memory 702 to DAC 704. For example, the memory 702 may be configured to be a look up table containing data corresponding to various waveforms. The desired set of data is selected by the controller 706, for example, in response to data received from the telemetry and impedance matching unit 106. The DAC 704 is configured to receive the desired data and to output an analog waveform in response. In another embodiment there is no memory 702, rather the controller 706 calculates the desired data to be used by the DAC 704.

Figure 8:
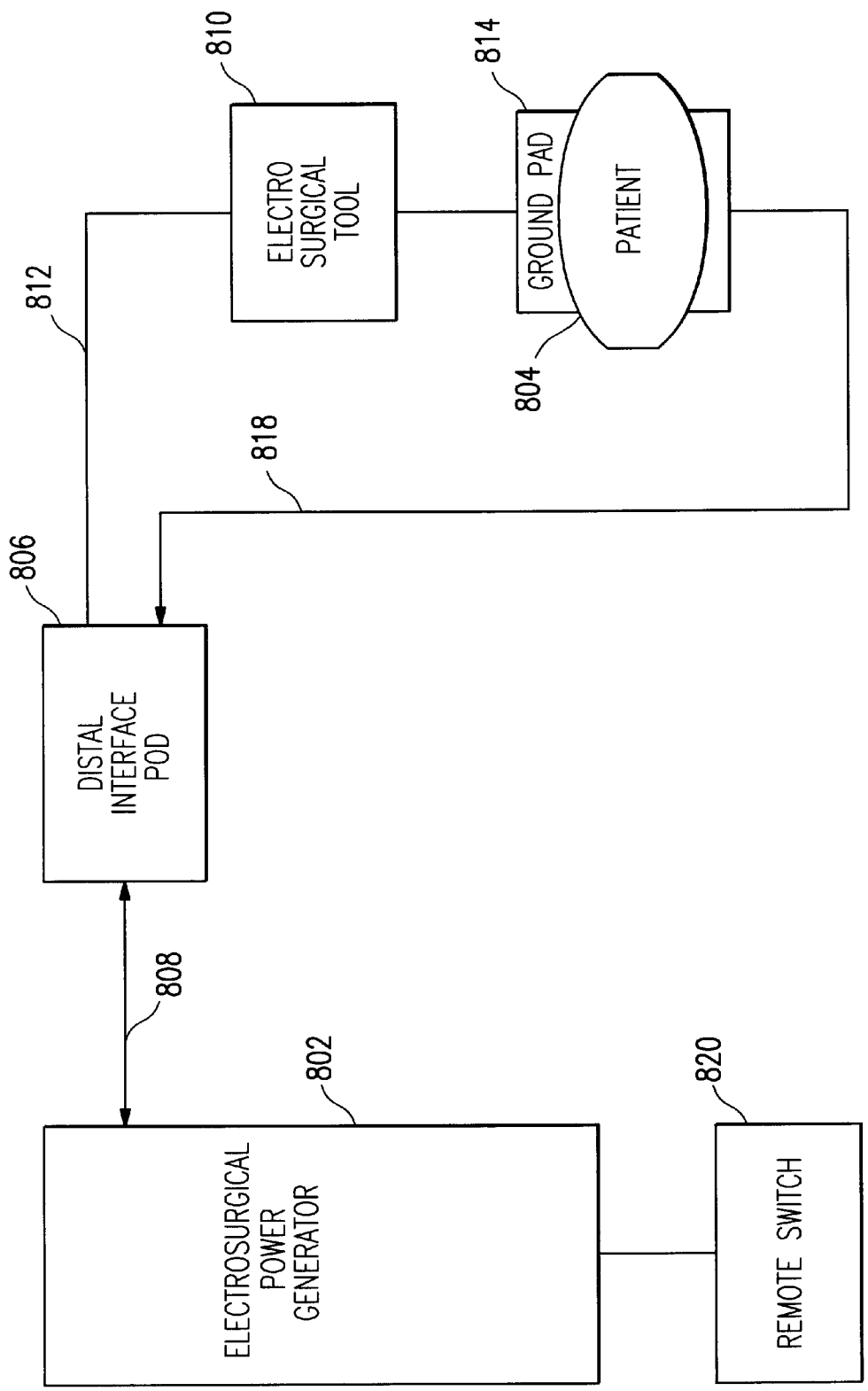
FIG. 8 is a representation illustrating the power signal path during an electrosurgical procedure.

FIG. 8 is a representation illustrating the power signal path during an electrosurgical procedure. An electrosurgical power generator 802 produces a desired output so as to effectively transfer electrical energy to the tissue of a patient 804 at a surgical site. In one embodiment, the output of the electrosurgical power generator is a radio frequency (RF) signal, such as, for example, an essentially sinusoidal waveform at about 5 MHz, at a power level of 450 to 650 watts. An essentially sinusoidal waveform may be, for example, a waveform with less than about 5% total harmonic distortion (THD). In another embodiment, the electrosurgical power generator output may be an essentially sinusoidal waveform at about 5 MHz at a power level up to 1,000 watts. In yet another embodiment, the electrosurgical power generator output may be an essentially sinusoidal waveform at about 3.4 MHz. It is contemplated that the electrosurgical power generator output may be any specific frequency between about 1 MHz and about 14 MHz, and various power levels up to several kilowatts.

In one embodiment, the output of the electrosurgical power generator 802 is connected to a distal interface pod 806 via a shielded cable 808. The distal interface pod 806 is located in relatively close proximity to the patient 804. As described below, the distal interface pod 806 comprises various electrical components and circuits providing, such as, for example, impedance matching and sensing circuits. In another embodiment, there is no distal interface pod, with the output of the electrosurgical power generator connected directly to the electrosurgical tool 810.

The output of the distal interface pod 806, or the output of the electrosurgical power generator 802, is connected to the electrosurgical tool 810 via a flexible shielded cable 812. As described below, the flexible shielded cable 812 conducts the output of the distal interface pod 806 to the electrosurgical tool 810 providing shielding for the surgeon and patient from radiated emissions produced by the RF waveform. In addition, the flexible cable 812 reduces the force required by the surgeon in maneuvering the electrosurgical tool 810 thereby increasing the effectiveness with which the surgeon can manipulate the electrosurgical tool 810.

During an electrosurgical procedure a surgeon will maneuver the electrosurgical tool 810 about the patient 804 to produce the desired results. The electrosurgical power generator procedures an electrical current that flows from the electrosurgical tool 110, through the patient 804 to a ground pad 814. The ground pad 814 is connected to the electrosurgical power generator 802 via the distal interface pod 806 to complete an electrical circuit. In addition, a pad sense circuit, in the distal interface pod 806, provides a mechanism for detecting that the ground pad is properly positioned to the patient.

Typically, due in part to the limited area available and the number of people involved, during an electrosurgical procedure the electrosurgical power generator 802 will be at a remote location, away from the patient, perhaps in a room separated from the operating room. A remote switch 820 in the operating room may be used providing the surgeon control of when the electrosurgical power generator outputs power to the electrosurgical tool 810 as well as whether to provide cut, coagulation or blend energy. In one embodiment, the remote switch 820 may be a foot activated switch. In other embodiments, other types of remote switches may be used, such as, for example, a voice activated switch or a push button located on the electrosurgical tool 810, or other related control equipment.

Figure 9:
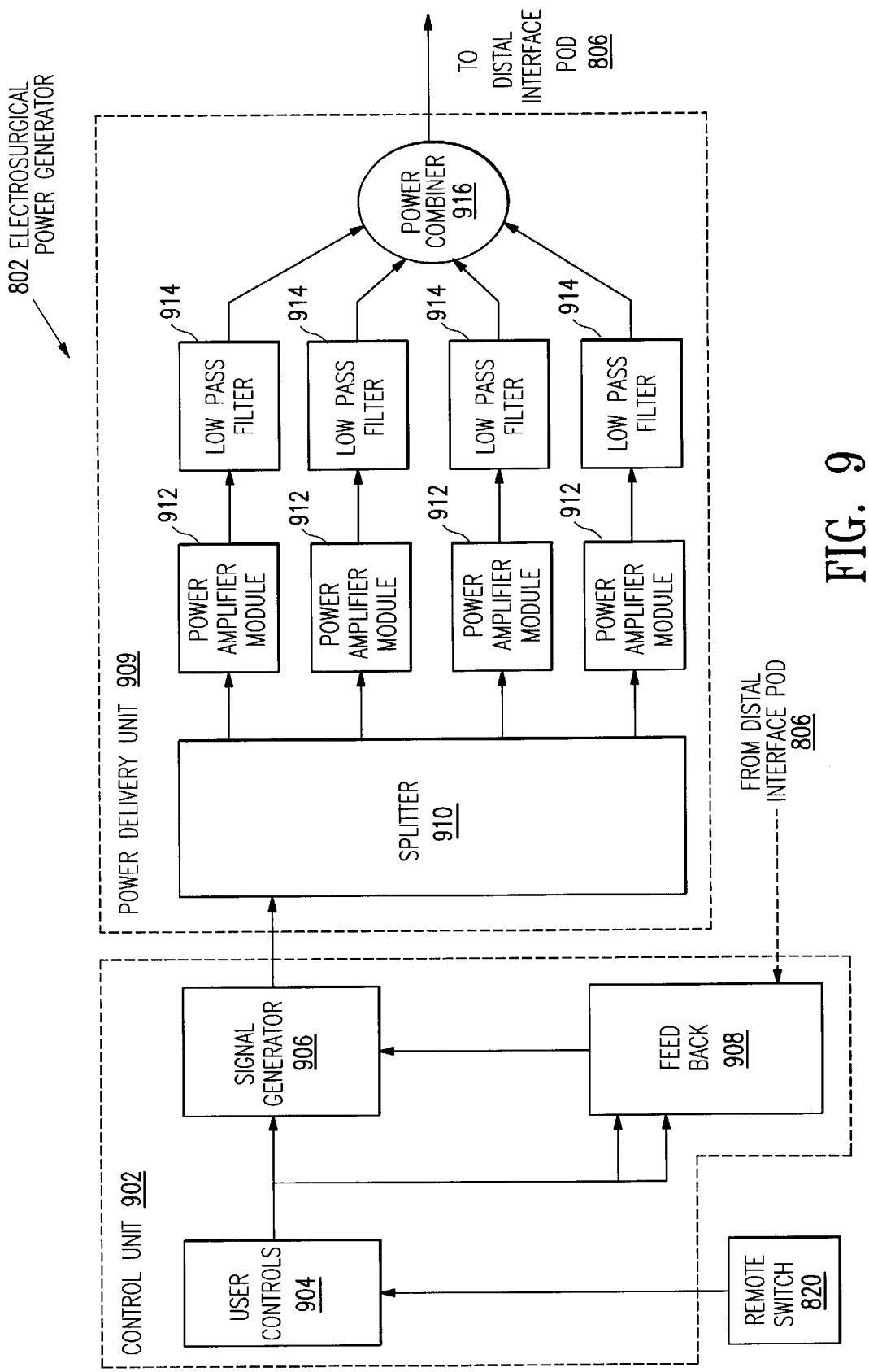
FIG. 9 is a block diagram of one embodiment of an electrosurgical power generator.

FIG. 9 is a block diagram of one embodiment of a electrosurgical power generator 802. A control unit 902 produces a control signal used to control a desired output from the electrosurgical power generator 802. The control unit includes user controls 904 allowing a user to select specific, desired setting of the control signal. In one embodiment, the user inputs desired setting via, such as, for example, a keyboard, keypad, touch screen, switches, rotary devices or any combination of these types of devices.

In one embodiment, the user controls 904 allow the user to select a desired frequency of the control signal output to the electrosurgical power generator 802. For example, the user controls may allow selection of an output frequency of 5 MHz or 3.4 MHz. In another embodiment, other parameters of the control signal may be selected by the user, such as, for example, output power level, output voltage level, output current level, duty cycle and gating controls of the output signal. User controls 904 may also receive input from a remote switch 820 allowing remote operation of the electrosurgical power generator 802. Adjustment of the above parameters allows for different modes of operation such as cut, coagulation and blend.

The output of the user controls is in communication with the signal generator 906 and the feedback circuit 908. The signal generator 906 produces a representation of the desired output of the electrosurgical power generator 802. The signal generator 906 is configured to accept input from the user control 904, and the feedback circuit 908, and modify its output accordingly. The signal generator 908 output is a low power signal used to control at least one power amplifier.

The feedback circuit 908 is configured to accept signals from the user controls 904 and the distal interface pod 806. Signals from the distal interface pod 806 may include signals for sensing various parameters of the RF waveform at the distal interface pod 806, such as, for example current and voltage present at the electrosurgical tool 810. The feedback circuit 908 outputs a signal to the signal generator 906 such that signal generator output controls at least one power amplifier to produce a desired waveform to the electrosurgical tool 810, as indicated by sensing parameters of the RF waveform at the distal interface pod 806.

The output of the control unit is in communication with the power delivery unit 909. The power delivery unit 909 is configured to receive the output of the control unit and produce a desired RF power output that is transmitted to an electrosurgical tool for use in an electrosurgical procedure.

In one embodiment, the power delivery unit 909 includes a single power amplifier module 912. In other embodiments, different numbers of power amplifier modules 912 may be included in the power delivery unit 909. For example, power delivery unit may include two, four, eight, or another number of power amplifier modules 912. In embodiments that include more than one power amplifier modules 912, the power delivery unit 909 may also include a splitter 910, and a power combiner 916.

The power delivery unit 909 illustrated in FIG. 9 includes four power amplifier modules 912. In this embodiment, the output of the control unit 902 is in communication with a splitter 910. The splitter 910 receives the low power output signal from the control unit 902, buffers the signal, and outputs a plurality of duplicate signals, one for each power amplifier module 912, of the same magnitude and characteristics as the signal from the control unit. In this embodiment the splitter 910 outputs four duplicate signals. Each of the duplicate outputs of the splitter 910 is connected to an individual power amplifier module 912. The power amplifier modules 912 are configured to receive a low power signal, and amplify the signal to a desired power level.

In one embodiment the power amplifier module 912 is an RF power amplifier, such as, for example, an LCF Enterprises part number 30-1-150-35-ES, or an equivalent RF power amplifier, adapted to produce the desired frequency, for example, about 1 MHz to about 10 MHz, specifically about 3 MHz to about 8 MHz, and more specifically about 3.4 MHz to about 5 MHz.

In one embodiment, the power amplifier 912 is an AB linear amplifier. In another embodiment, the power amplifier 912 is a class AB amplifier. In other embodiments the power amplifier 212 may be a class E, class B, class C or class D amplifier. In another embodiment, the power amplifier 912 outputs an essentially sinusoidal waveform with less than about 5% total harmonic distortion (THD).

In one embodiment, each of the high power output of each power amplifier module 912 is connected to a filter 914. Each filter 914 is configured to accept the output of the power amplifier module 912 and eliminate undesired spectral components. For example, the filter 914 may be a low pass filter with a corner frequency of about MHz, a rolloff of about 24 dB per octave. In another embodiment, various parameters of the filter are selected so that the output waveform is such that subsequent matching and telemetry isolation transformers perform adequately. In another embodiment, the filter 914 is a bandpass filter centered at about the fundamental frequency of signal generator 906.

Each of the filters 914 outputs are connected to a power combiner 916. The power combiner 916 is configured to accept the outputs from the plurality of power amplifiers 912. In one embodiment, the power combiner 916 is configured to accept four independent power signals. The independent power signals are summed in the power combiner 916 into one power signal. The output of the power combiner 916 is transmitted to the distal interface pod 806 via the shielded cable 808. In an embodiment where a single power amplifier is used, then a power combiner is not necessary.

Figure 10:
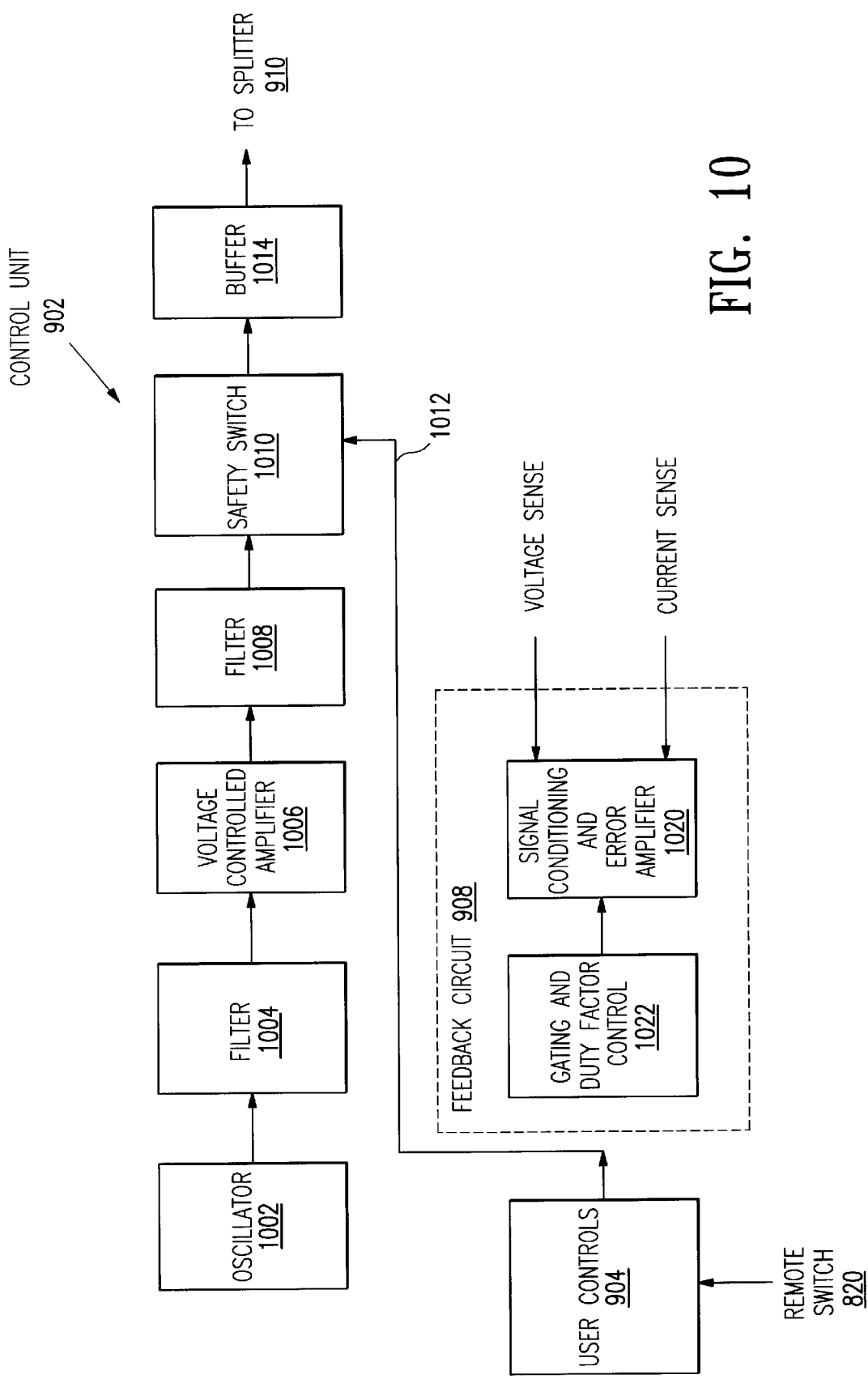
FIG. 10 is a block diagram that shows additional details of one embodiment of a control unit.
Figure 11A:
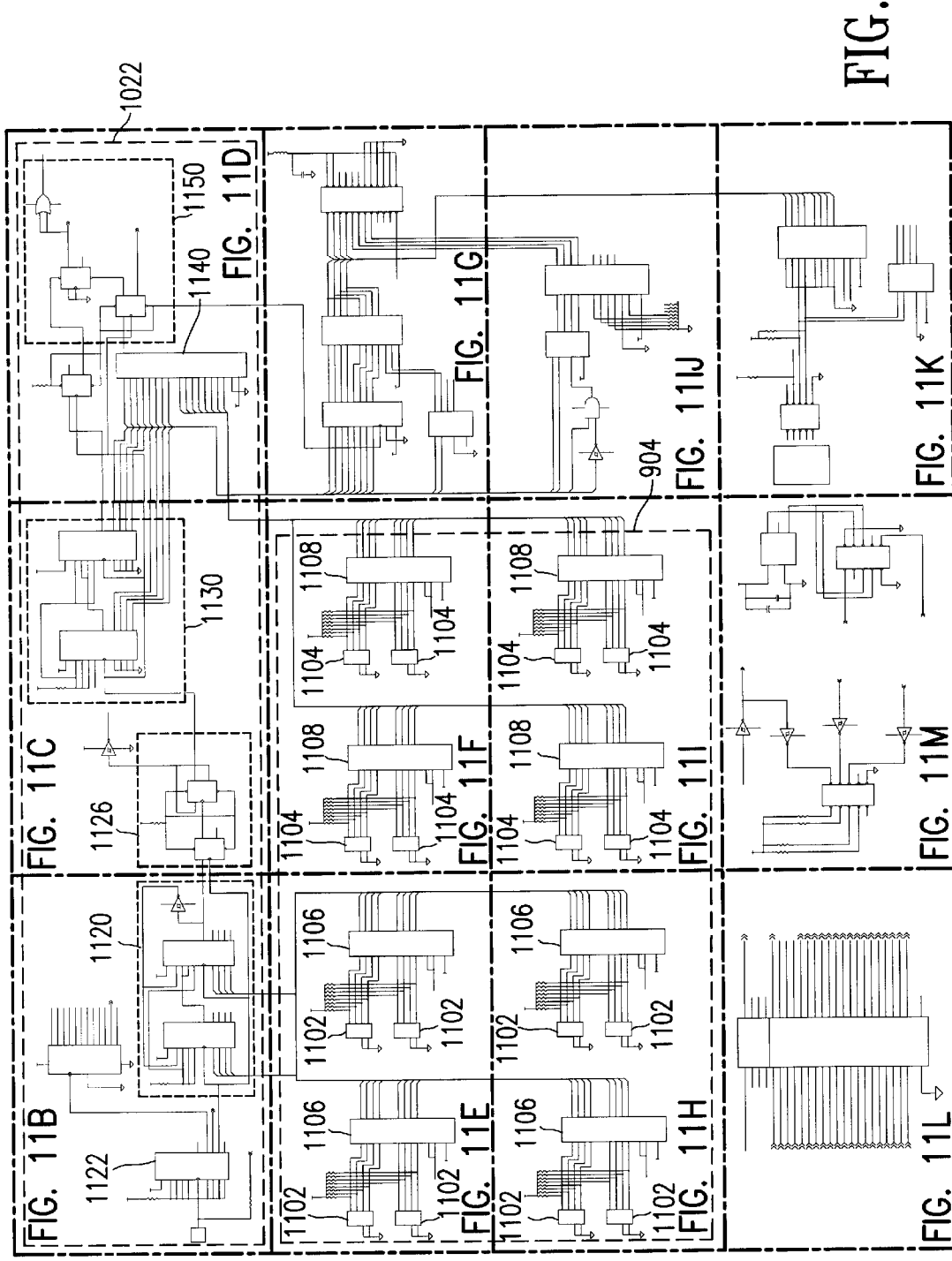
FIG. 11 is a block diagram showing additional detail of portions of user controls and gating and duty factor control.
Figure 11D:
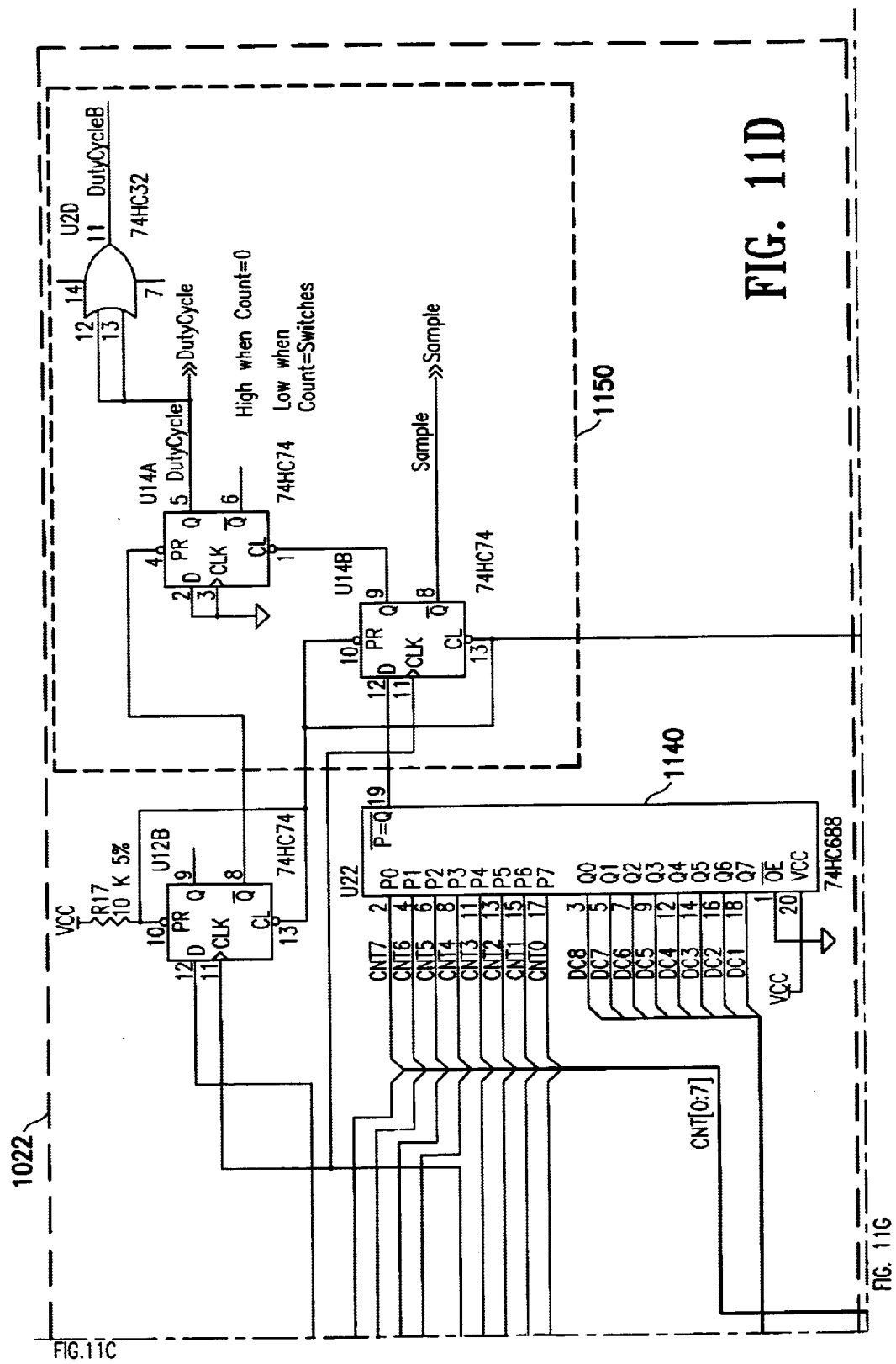
Figure 11G:
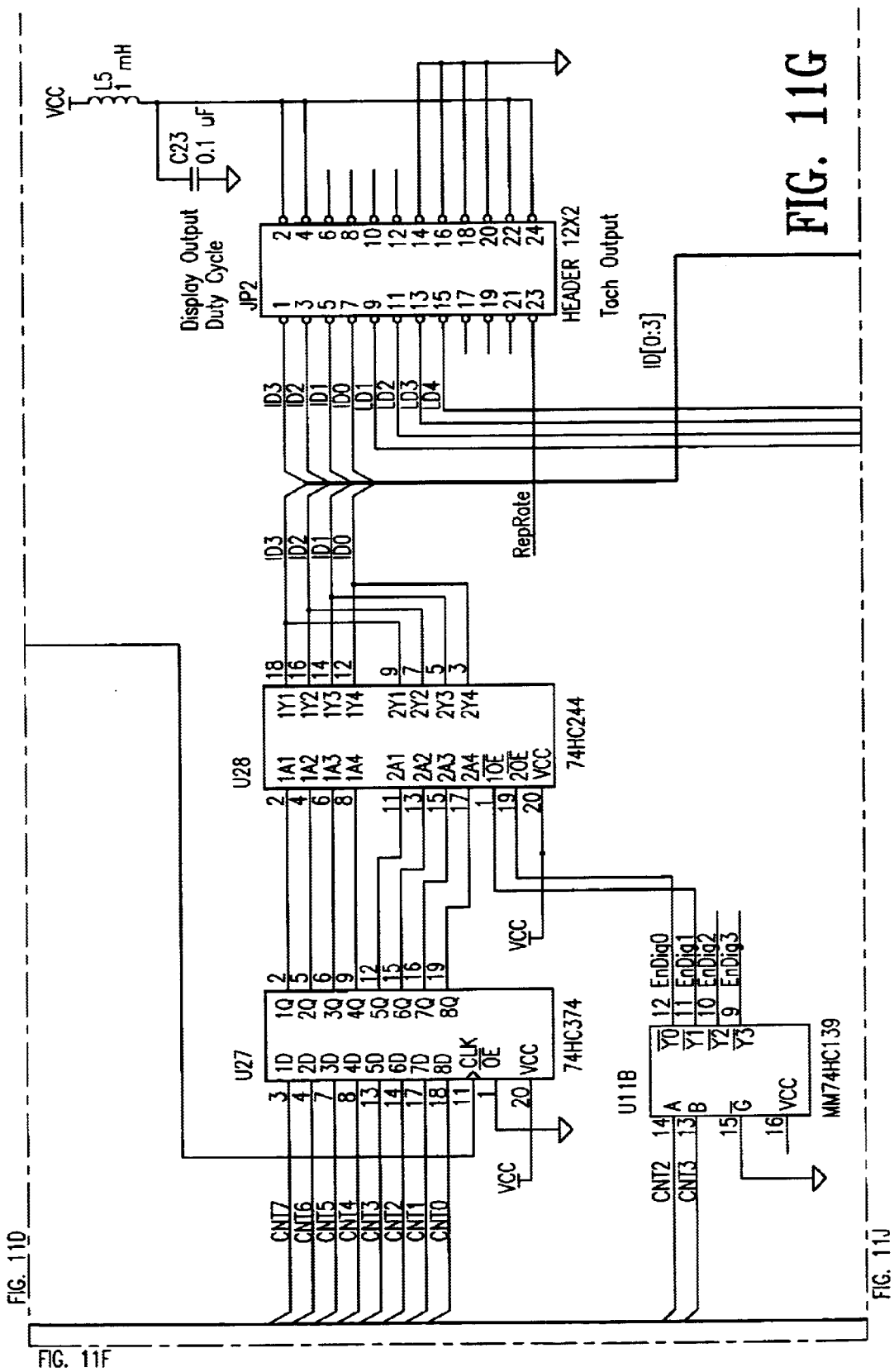
Figure 11H:
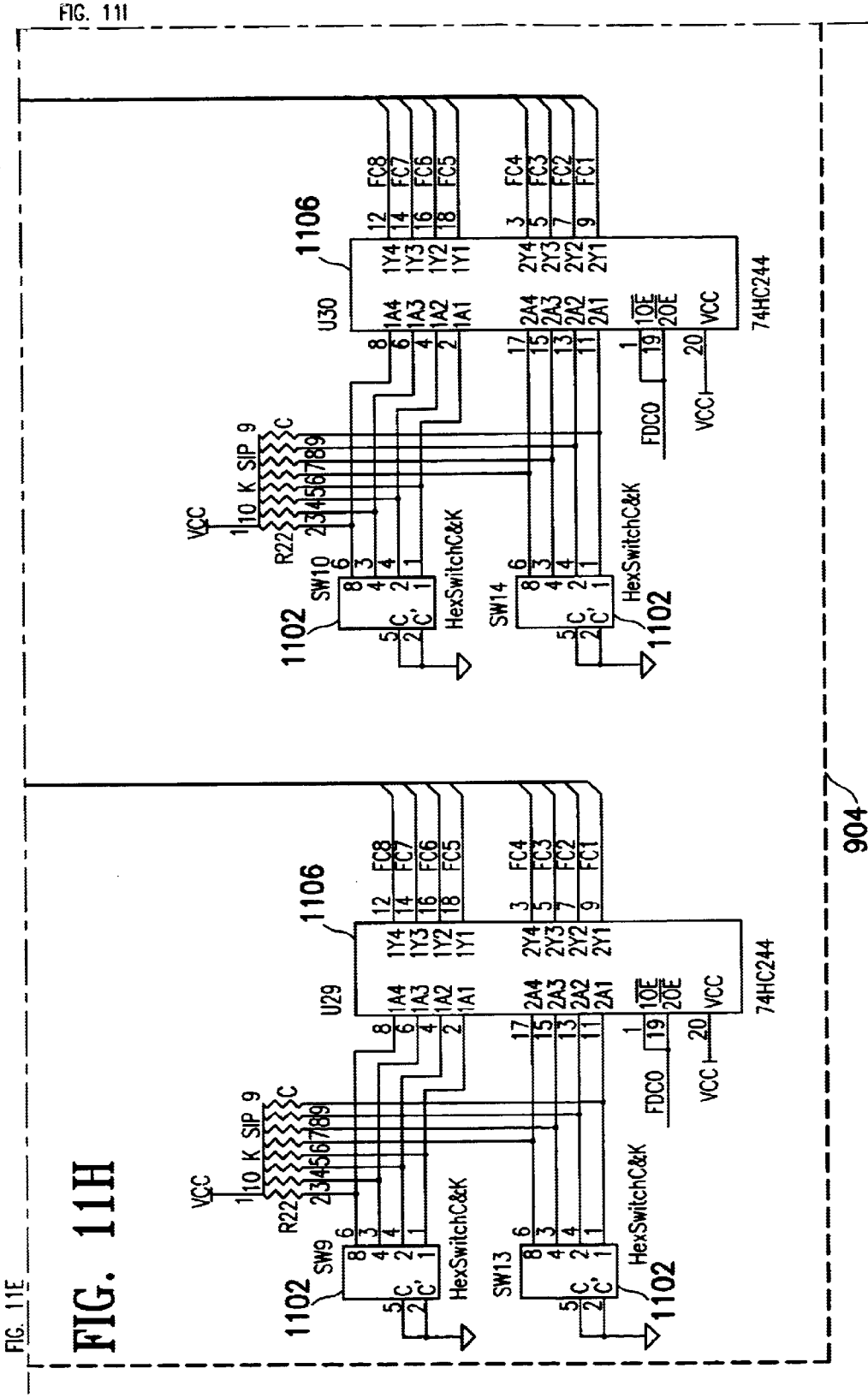
Figure 11J:
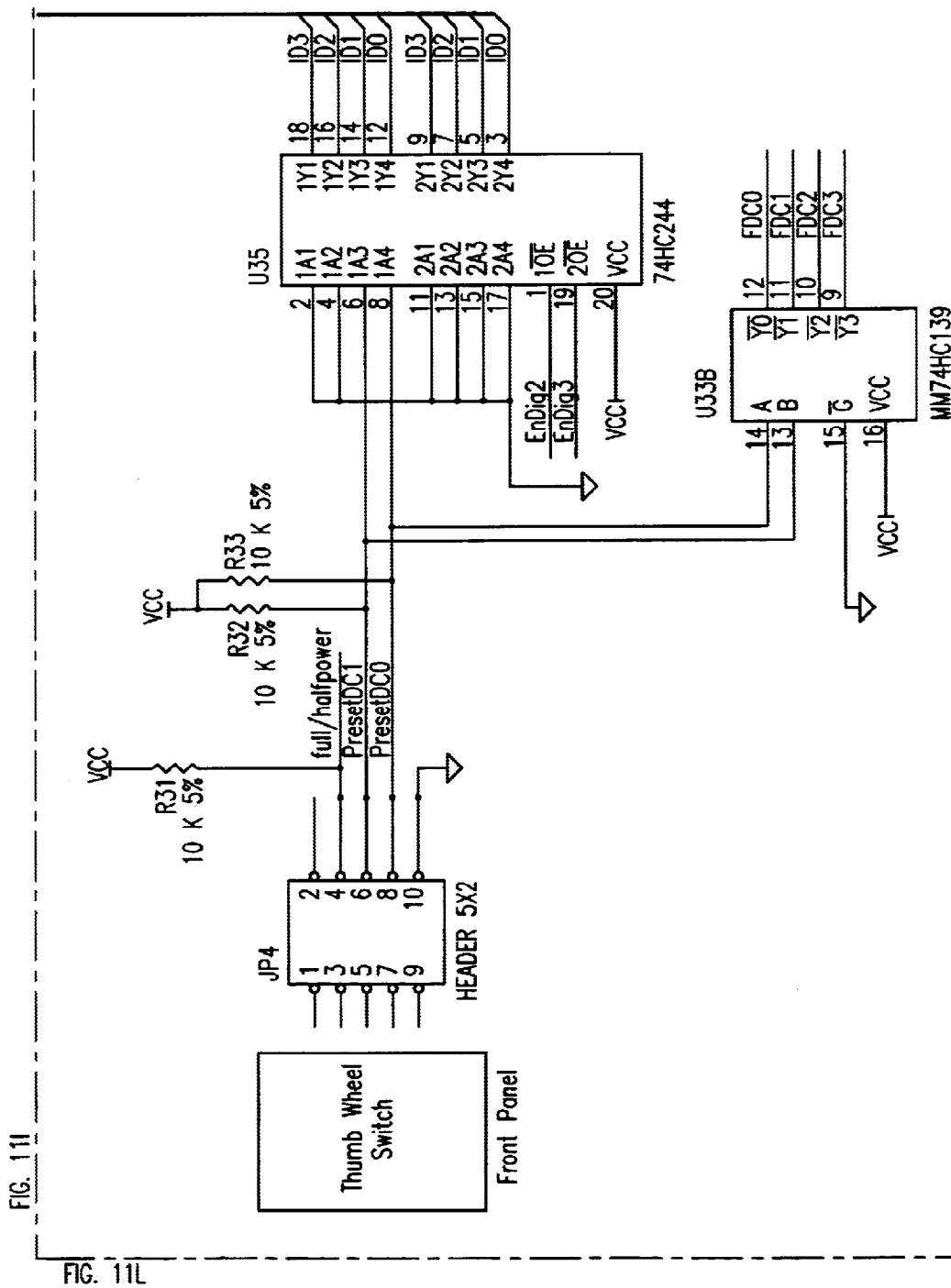
Figure 11K:
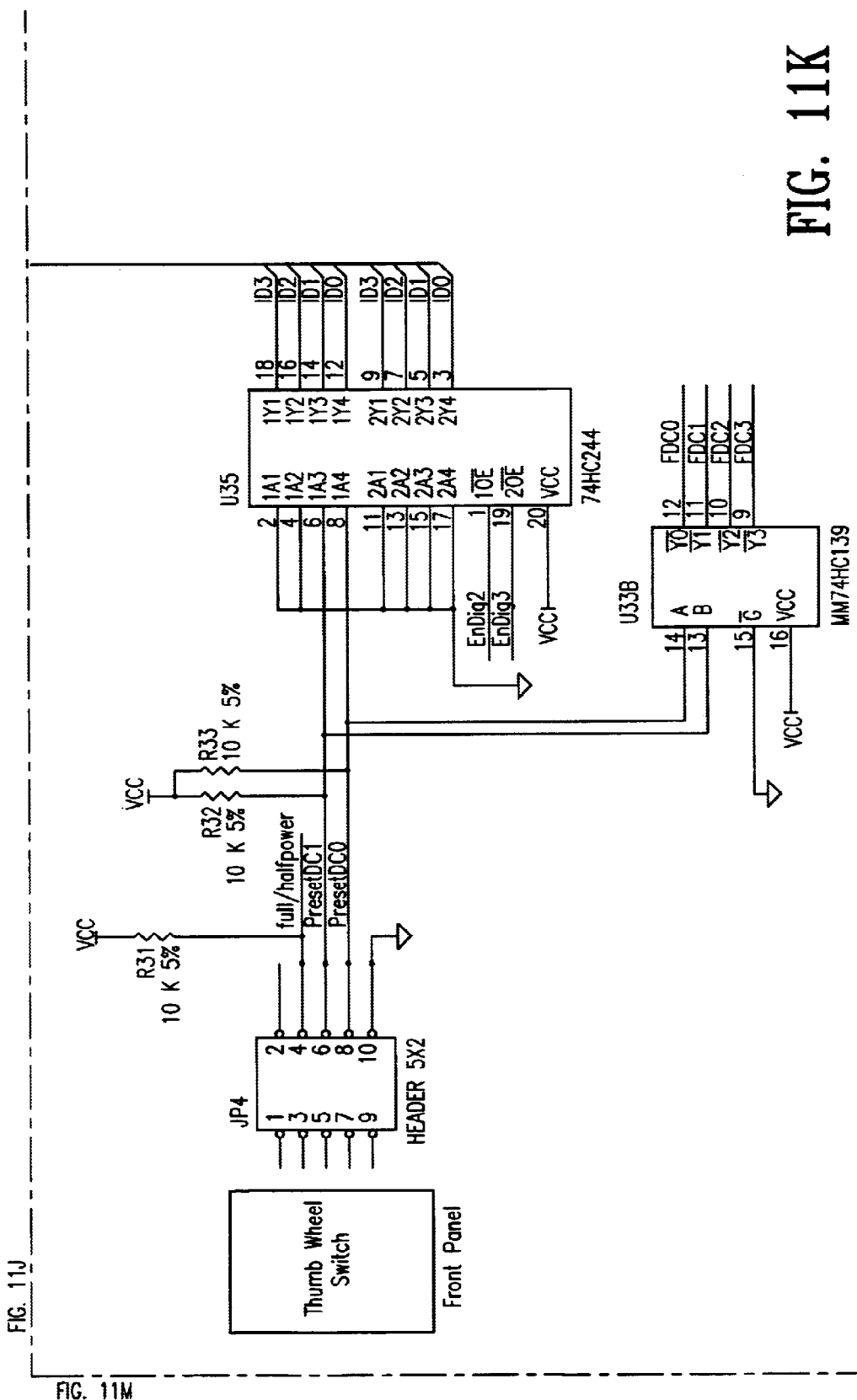
Figure 12A:
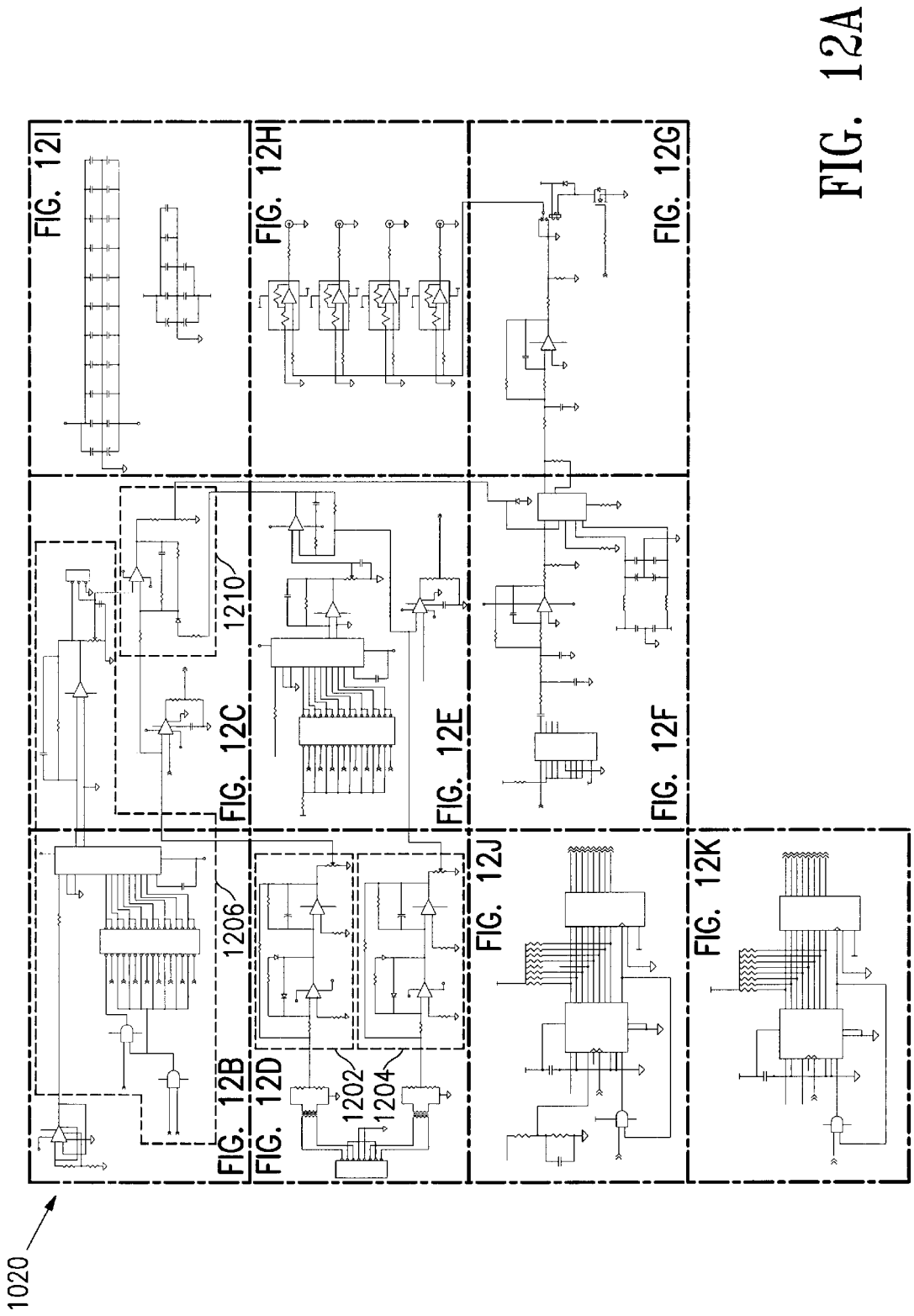
FIG. 12 is a block diagram showing additional detail of portions of signal conditioning and error amplifier.
Figure 12B:
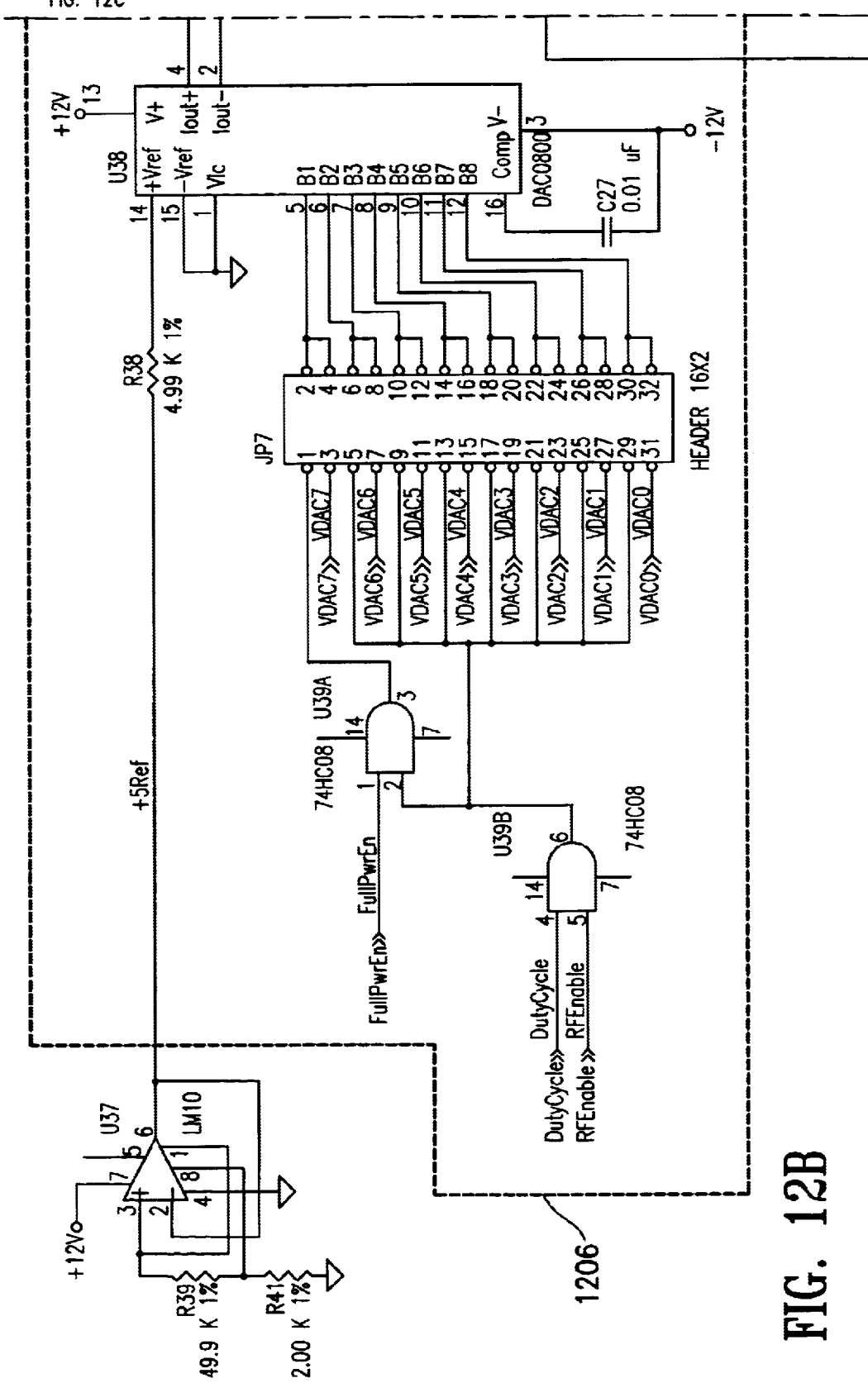
Figure 12C:
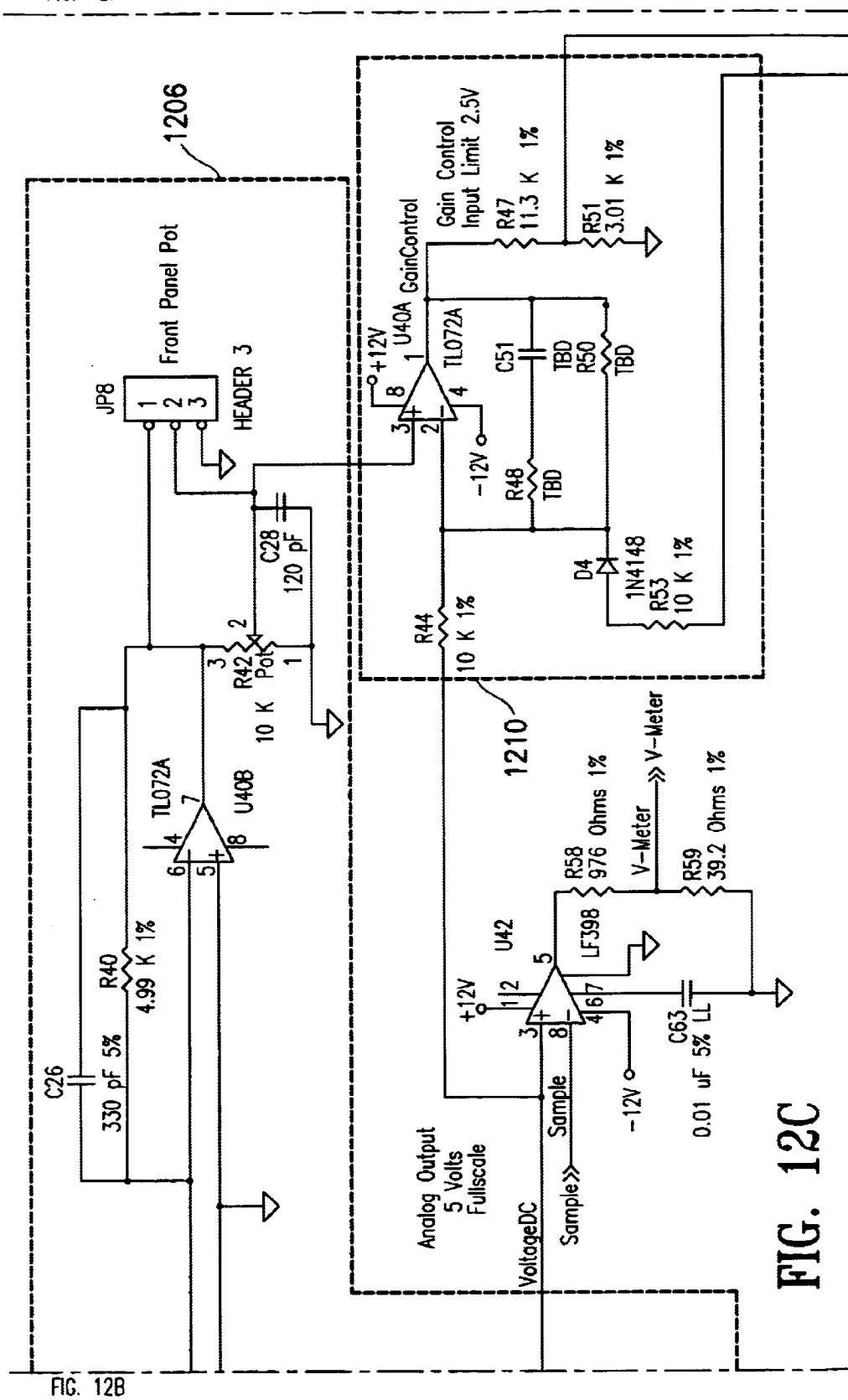
Figure 12D:
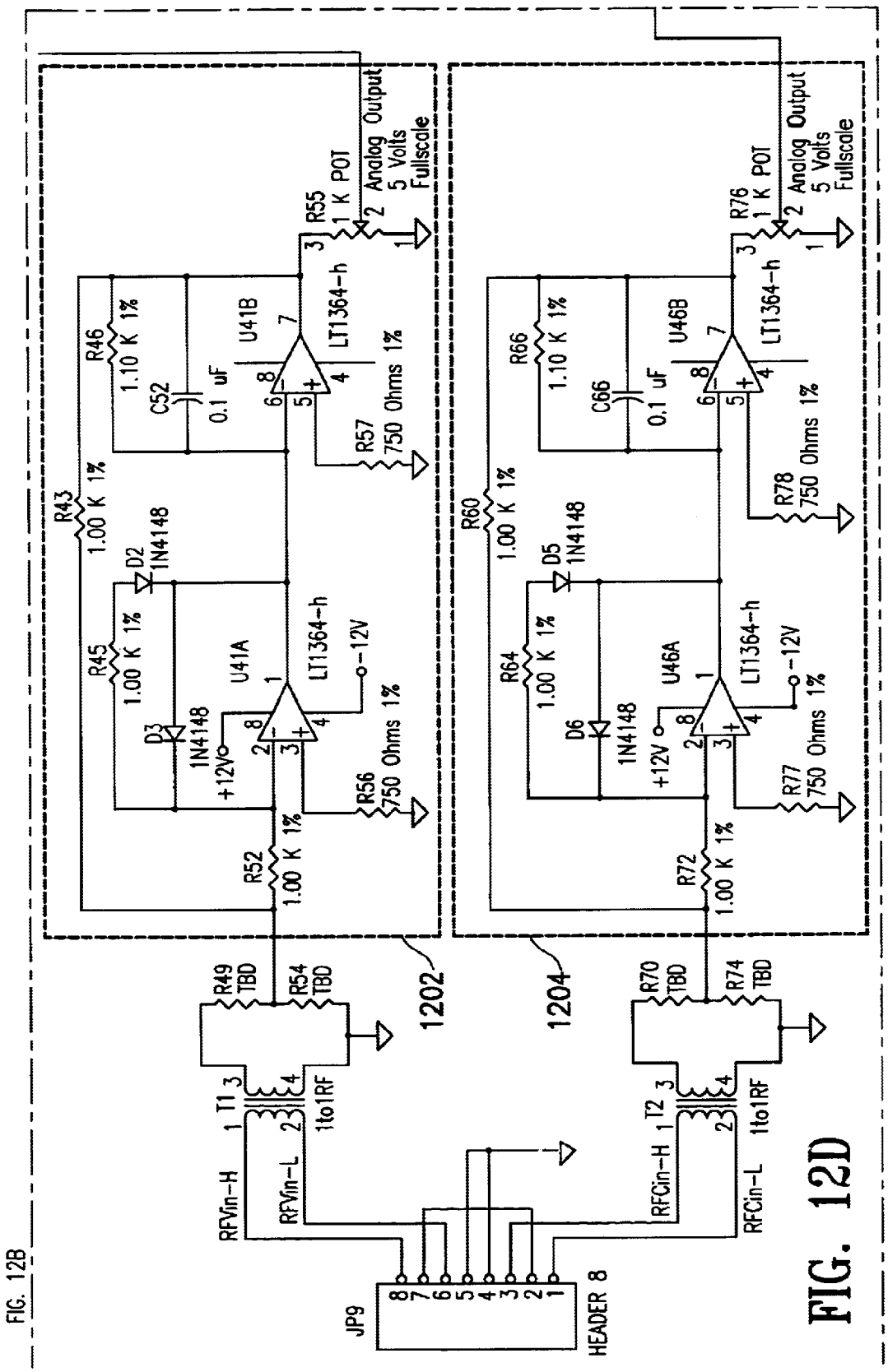
Figure 12F:
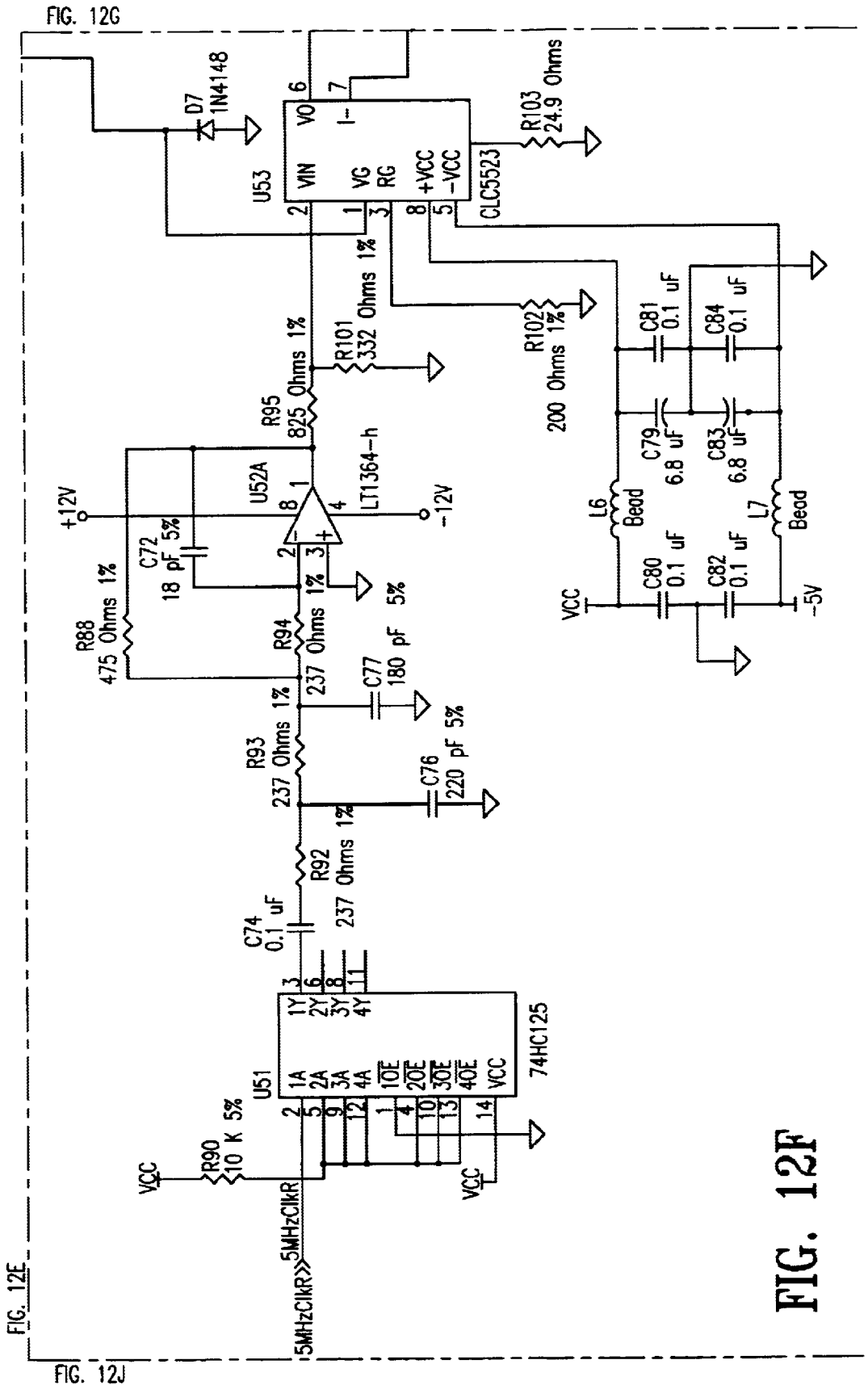
Figure 12G:
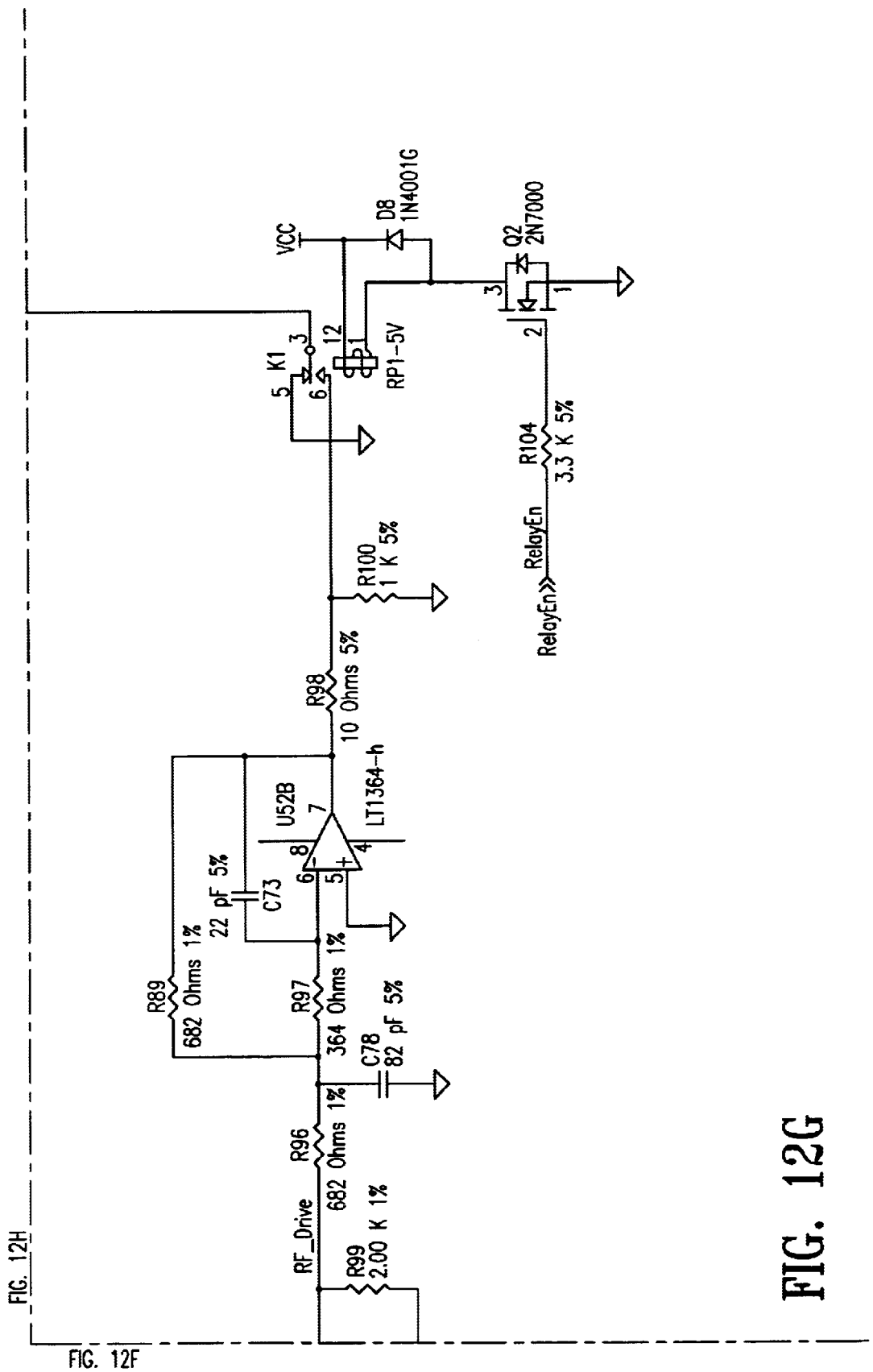
Figure 12H:
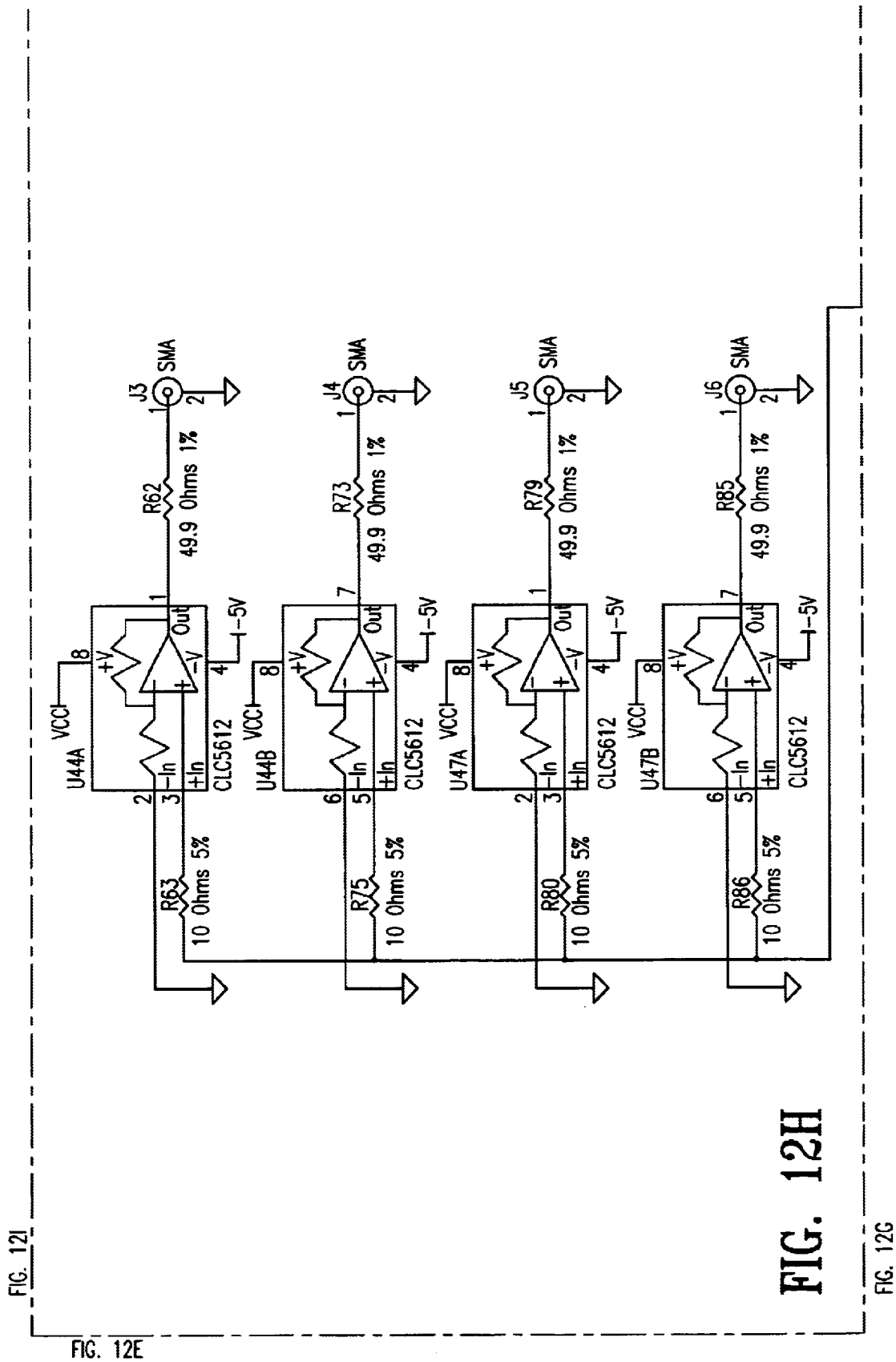
Figure 12I:
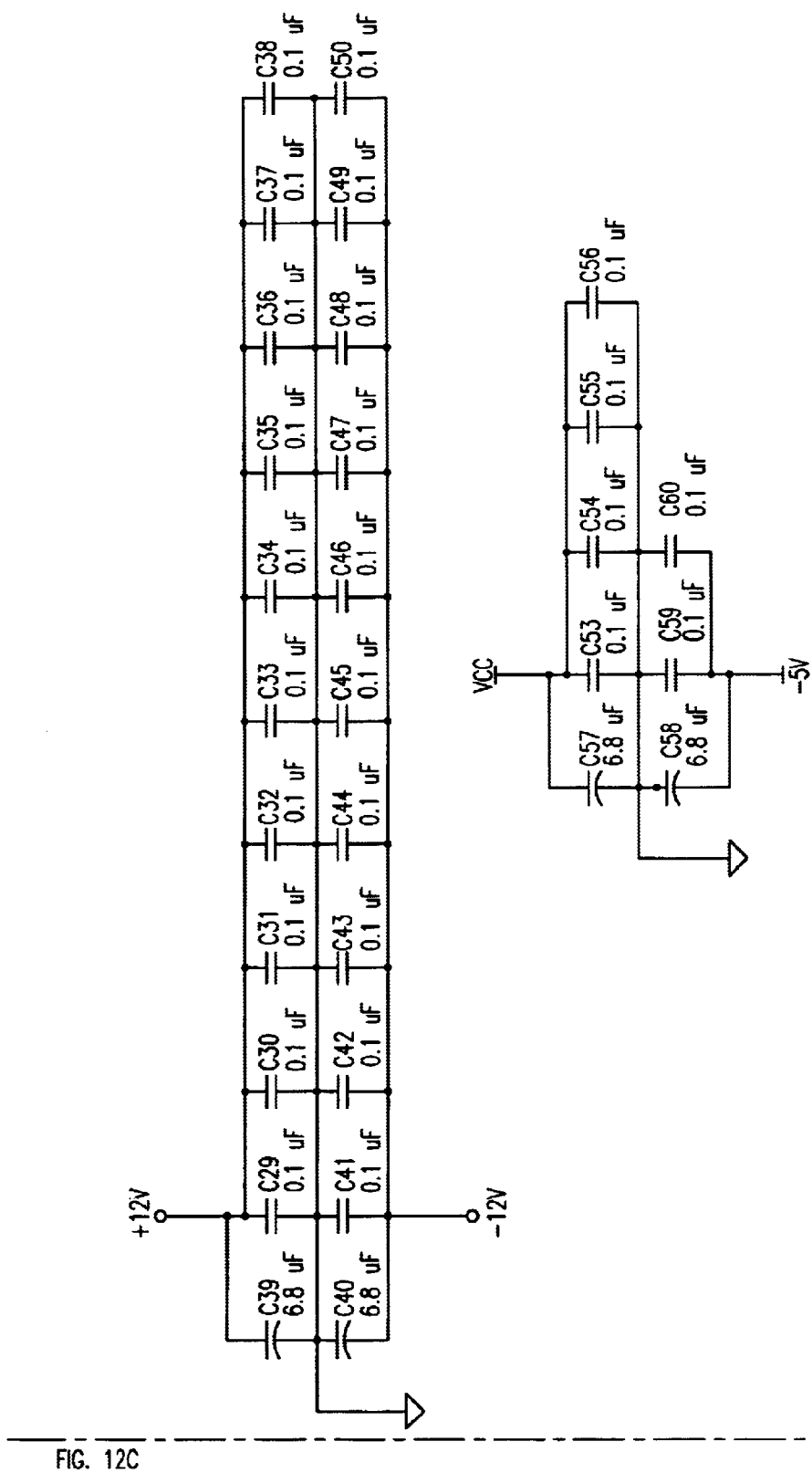
Figure 12J:
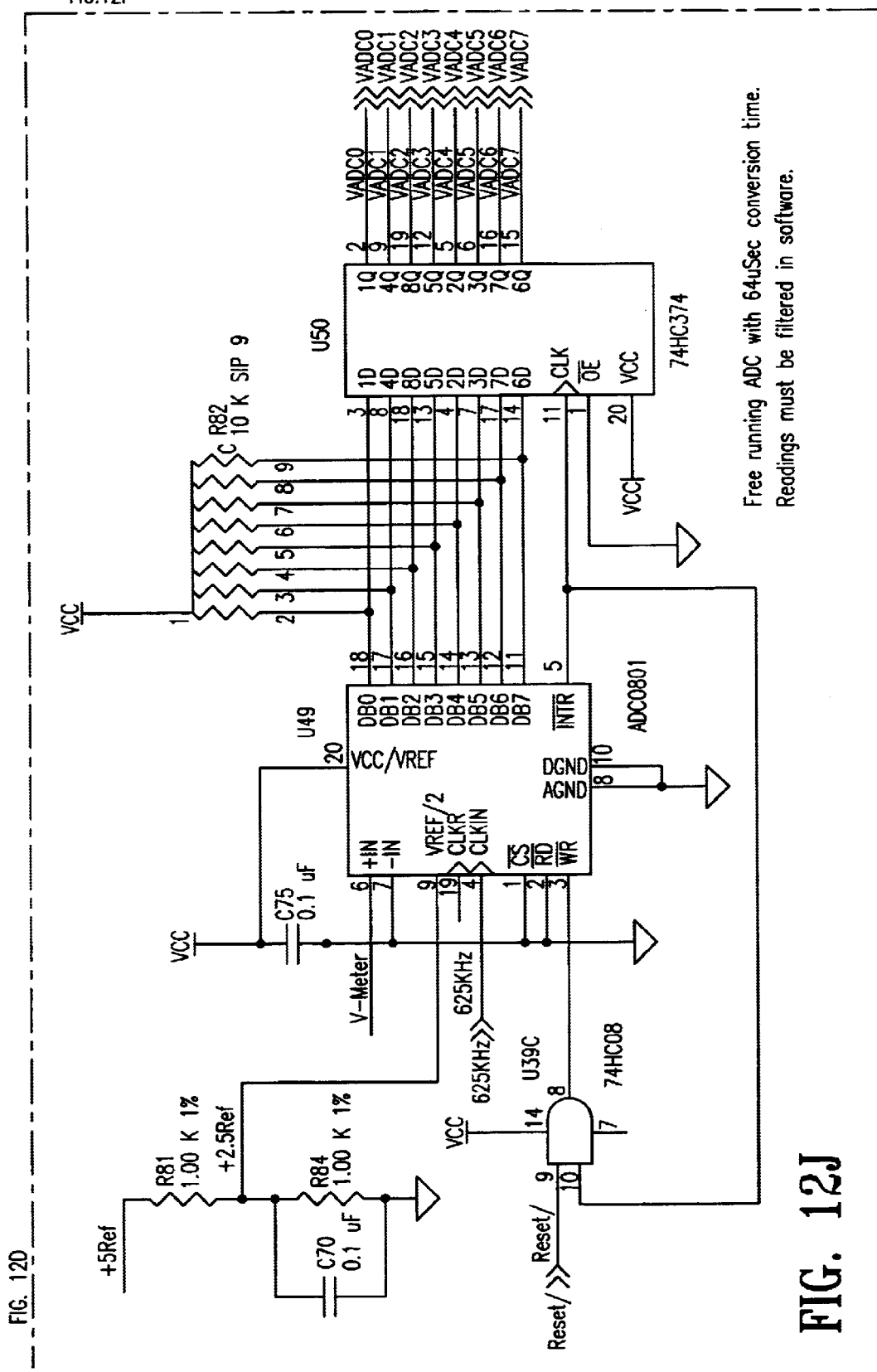
Figure 12K:
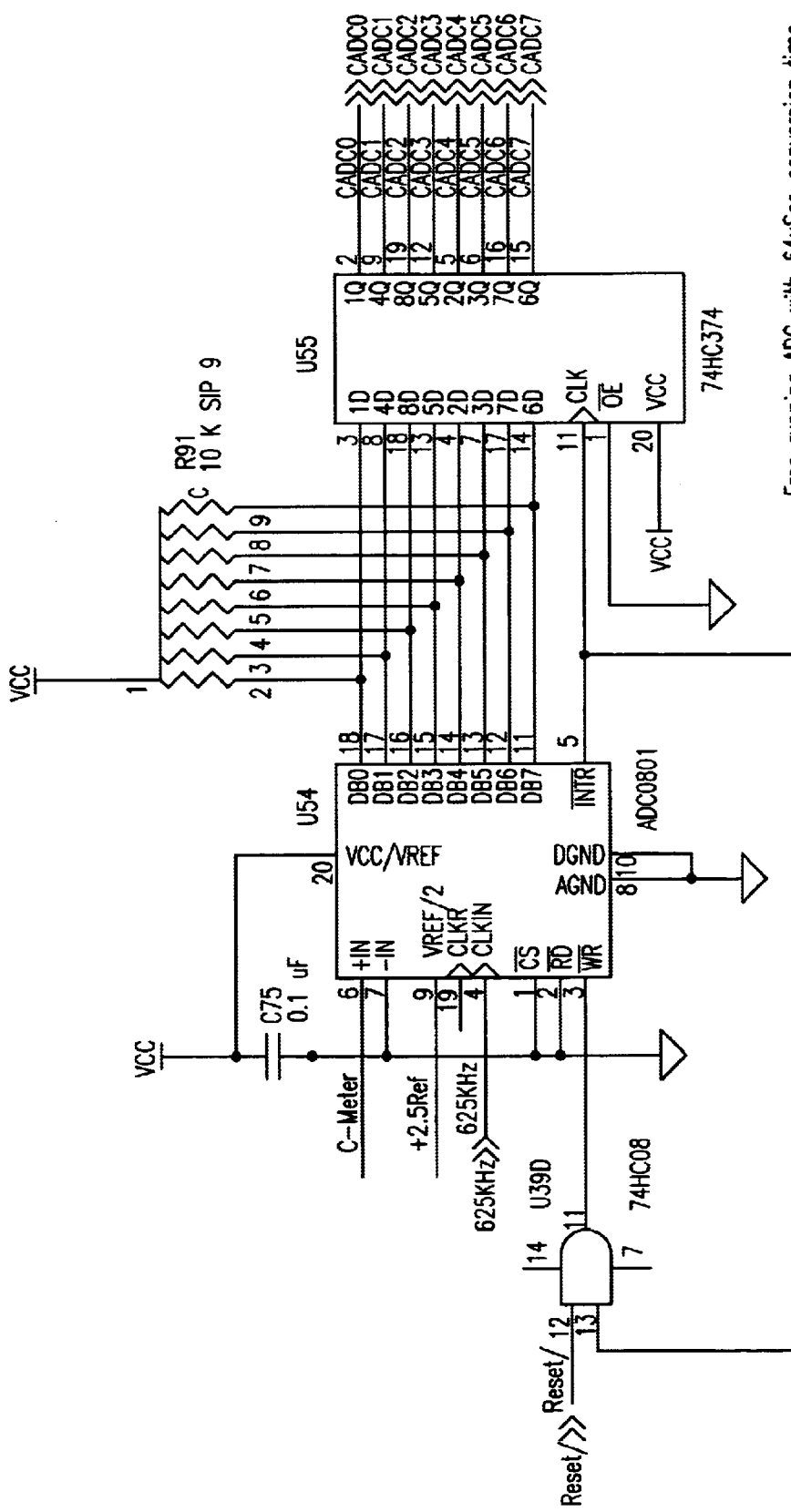

FIG. 10 is a block diagram that shows additional details of one embodiment of a control unit 902. The control unit 902 includes an oscillator 1002. The oscillator 1002 generates a waveform at a desired frequency. Generally, the oscillator is configured to output a periodic waveform. In one embodiment, the oscillator 1002 produces square waveform of about 5 MHz. In another embodiment, the oscillator 1002 produces sinusoidal waveform of about 5 MHz. In other embodiments, the oscillator 1002 produces square waveforms or sinusoidal waveforms at different frequencies from about 1 MHz to about 14 MHz, specifically about 3 MHz to about 8 MHz, and more specifically about 3.4 MHz to about 5 MHz. In yet another embodiment, the oscillator may be the scaled output of a higher frequency signal, for example, a 40 MHz clock divided by 8 to produce a 5 MHz squarewave. The oscillator output may be connected to a filter 1004.

The filter 1004 is configured to receive the output of the oscillator 1002. In one embodiment, the filter 1004 is configured as a low pass filter with a corner frequency of about 7 MHz, a rolloff of approximately 12 dB per octave. In another embodiment, the filter 1004 is a bandpass filter centered at about the fundamental frequency of oscillator 1002.

The filter 1004 is configured such that only the fundamental frequency of the oscillator 1002 waveform passes through the filter, with most, or all, harmonics of the fundamental frequency being attenuated. Thus, if the output of the oscillator is a square waveform, the output of the filter 1004 will be a sinusoidal waveform at the fundamental frequency of the oscillator 1002. If the output of the oscillator 1002 is a sinusoidal waveform, the output of the filter 1004 will also be a sinusoidal waveform at the fundamental frequency of the oscillator 1002. The output of the filter 1004 is connected to a voltage controlled amplifier 1006. The voltage controlled amplifier 1006 is configured to receive the essentially sinusoidal waveform output from the filter 1004. In addition, the voltage controlled amplifier 1006 is configured to receive a control signal from the feedback circuit 908. The control signal may vary the gain of the voltage controlled amplifier 1006. In one embodiment, the voltage controlled amplifier 1006 amplifies the waveform output by the filter 1004. In another embodiment, the voltage controlled amplifier 1006 attenuates the waveform output by the filter 1004.

In one embodiment, the output waveform of the voltage controlled amplifier 1006 is connected to a filter 1008. The filter 1008 attenuates harmonics, or other undesired signals, that may have been generated during manipulation of the waveform in the voltage controlled amplifier 1006. In one embodiment, the filter. 1008 is a low pass filter with a corner frequency of about 7 MHz, a rolloff of approximately 12 dB per octave. In another embodiment, the filter 1008 is a bandpass filter centered at about the fundamental frequency of oscillator 1002, attenuated about 3 dB at approximately ±250 kHz from the fundamental frequency, and attenuated about 12 dB/octave It is desirable to select filter parameters so that there is steep attenuation of frequencies that are out of band of the filter.

The output of the filter 1008 is connected to a safety switch 1010.

The safety switch 1012 either passes the waveform received from the filter 1008 on to a buffer amplifier 1014, or blocks the waveform, preventing it from reaching the buffer amplifier 1014 in response to a safety control signal. In one embodiment, a safety control signal 1012 operates the safety switch 1010 in response to the remote switch 820. When the remote switch 820 is activated the safety switch will pass the waveform to the buffer amplifier 1014. When the remote switch 820 is inactivated the safety switch 1012 will block the waveform from buffer amplifier 1014. In one embodiment, the safety switch 1010 is a relay. In other embodiments the safety switch may be an active component, such as, for example, bipolar or MOS transistors configured as gatable clamps. In addition, photo-resistors can be configured to perform the switch function as well as CMOS or MOS analog switch integrated circuits.

The output of safety switch 1010 is connected to the buffer amplifier 1014. The buffer amplifier 1014 is configured as a unity gain amplifier used to improve the electrical load drive capability of the control unit 902. In one embodiment, buffer amplifier 1014 is a high output drive current buffer, such as, for example, National Semiconductor CLC5612. The output of the buffer amplifier 1014 is connected to the splitter 910.

The feedback circuit 908 includes a signal conditioning and error amplifier 1020, and a gating and duty factor control 1022. The signal conditioning and error amplifier 1020 produces a control signal that controls the gain of the voltage controlled amplifier 1006. The signal conditioning and error amplifier 1020 control signal varies in response to sensing and control inputs to the signal conditioning and error amplifier 1020. In one embodiment, the voltage and current at the electrosurgical tool 810 are sensed and transmitted to the signal conditioning and error amplifier. In addition, the user controls 904 may allow a user to select desired voltage and current settings for an electrosurgical procedure. For example, a user may select a maximum current level that is not to be exceed, or a desired voltage level that is desired to be maintained. Additionally, the user controls 904 may allow a user to select desired gating and duty factor settings. Aspects of voltage and current levels, as well as gating and duty factor on electrosurgical procedures, is discussed further below.

As discussed above, for electrosurgical cutting to be effective an adequate, or critical voltage must be present at the cutting electrode to sustain the vapor, or gas, barrier in a conductive state. If the voltage present at the cutting electrode reduces to a level below the critical voltage level, the vapor barrier will stop conducting, and cutting will cease. Regulation of the electrosurgical power generator to maintain the voltage present at the cutting electrode at a level above the critical level is accomplished by monitoring the voltage present at the electrosurgical tool 810 as well as the DC potential generated across the tool/tissue boundary and adjusting the gain of the voltage controlled amplifier 1006 accordingly.

In addition, regulation of the electrosurgical power generator output voltage can prevent the output voltage from increasing substantially when tissue characteristics reduce the amount of current drawn from the generator. Limiting the voltage output of the electrosurgical power generator limits the energy transferred to the tissue and therefore reduces the risk of collateral damage to tissue during the electrosurgical procedure.

The cutting current varies in response to tissue impedance changes. Lower impedance tissue, such as muscular or glandular tissue, has higher conductivity than higher impedance tissue such as fat, and therefore generally requires less sustaining voltage to produce the same amount of current. Factors that affect the impedance once cutting has begun include the electrode area and the conductance of a plasma layer generated during the cutting process. A sustaining voltage, that varies as different tissue types are encountered, is needed to maintain the current density over the electrode area.

Regulating, or limiting, output current from the electrosurgical power generator will reduce variations in the amount of current passed through the tissue as the electrosurgical tool 810 encounters tissue with different impedance while cutting. Current regulation will reduce the amount of current passed through the tissue when lower impedance tissue is encountered and increase the amount of current, up to a preset current limit, when higher impedance tissue is encountered.

The gating and duty factor control 1022 is in communication with the user controls 904, and the signal conditioning and error amplifier 1020. In one embodiment, the gating and duty factor control 1022 modifies the waveform used to generate the electrosurgical power generator output. Gating refers to allowing the signal from the low pass filter 1004 to pass through the voltage controlled amplifier 1006. When the gate is "open", or "on", the signal passes through the voltage controlled amplifier 1006. When the gate is "closed", or "off", the signal does not pass through the voltage controlled amplifier 1006. Gating may be used to allow a "burst" of signal through the voltage controlled amplifier 1006. For example, the gating signal may turn on, and open the gate, allowing a desired number of cycles of the signal from the low pass filter 1004 through the voltage controlled amplifier 1008. The gate may then turn off, closing the gate, and block further signals from the low pass filter 1004 to pass through the voltage controlled amplifier 1006. In this manner, a burst of signals are allowed to pass through voltage controlled amplifier 1006.

Duty factor control refers to the ratio between the "on" and "off" periods of the gating signal. For example, a user may desire to have an output of the electrosurgical power generator 802 be a continuous sinusoidal wave of about 5 MHz that is modulated such that it appears as gated bursts at a controlled frequency when the remote switch is activated. The user may desire the output of the electrosurgical power generator 802 to alternate between "on" and "off" at a 100 Hz rate with the "on" period occupying 25% of the waveform period. To generate this waveform, the oscillator 1002 would generate a square wave or sine wave at 5 MHz. The oscillator 1002 output would pass through the low pass filter 1004. Output of the lowpass filter, a 5 MHz sine wave, will be passed to the voltage controlled amplifier 1006. The gating and duty factor control 1022 generates a signal, passed to the signal conditioning and error amplifier 1020, so as to generate a control signal that will gate the voltage controlled amplifier 1006 on and off at a 100 Hz rate, thus repeating every 10 msec. The desired 25% duty factoring means that the voltage controlled amplifier 1006 will be gated "on" for 2.5 msec, and then gated off for 7.5 msec.

Gating may also be performed at higher frequencies, for example 50 kHz, or up to the frequency of the signal being gated. Gating at higher frequencies may prevent subjecting the patient to frequencies within the biological passband and thereby decrease the possibility of neuromuscular stimulation.

Adjusting the waveform duty factor in this manner has several benefits, such as, for example, reducing the average power delivery to 25% of the power that would be delivered with a continuous waveform. Although the average power is reduced by 25%, the peak voltage of the waveform during the "on" portion is unchanged. Thus, duty factoring may allow for a sufficient voltage level to sustain cutting, while reducing the amount of energy delivered to the patient thereby reducing risks associated with excessive delivery of energy. Waveforms that can be used for coagulation and blending may also be produced by controlling parameters as described above.

In one embodiment, when duty factoring is being used, the waveshape envelope is controlled to produce a desired waveshape. For example, a waveshape envelope may be, for example, a ramped, or trapezoidal, rectangular envelope. In another embodiment, the waveshape may be, for example, a zero crossing switched rectangle. In other embodiments, different waveshape envelopes may be used to produce a desired signal.

FIG. 11 is a block diagram showing additional detail of portions of user controls 904 and gating and duty factor control 1022. In one embodiment, user controls 904 includes input switches. A first set of input switches 1102 allows the user to select a desired gating, or repetition rate, for the output of the electrosurgical power generator. The first set of input switches 1102 are buffered by a first set of logic buffer 1106 to isolate and enhance electrical drive capability to the input switches 1102 signals. A second set of input switches 1104 allows the user to select a desired duty factor for the output of the electrosurgical power generator. The second set of input switches 1104 are buffered by a second set of logic buffer 1108 to isolate and enhance electrical capability of the input switches 1104 signals.

The output of the first set of logic buffer 1106, the desired gating, or repetition rate setting is communicated to the gating and duty factor control 1022. The repetition rate setting is an 8 bit command that is connected to the data inputs of two presettable counters, a lower nibble counter and an upper nibble counter. The lower nibble counter and upper nibble counter are cascaded to produce a first 8 bit counter 1120. In one embodiment, the presettable counters are 74HC163 integrated circuits, or equivalent. The clock input to the counter 1120 is connected to another presettable counter 1122 configured to divide the main clock to a desired frequency. In one embodiment the main clock is 5 MHz and the counter 1122 is configured as a divide by four counter to produce a 1.25 MHz output used to clock the counter 1120. In one embodiment, the counter 1122 is a 74HC163 integrated circuit, or equivalent.

The ripple-carry output of the first 8 bit counter 1120 is connected to a D flip flop circuit 1126 that drives another set of presettable counters cascaded to produce a second 8 bit counter 1130. In one embodiment, the presettable counters are 74HC163 integrated circuits, or equivalent. The data outputs of the second 8 bit counter 1130 are connected to a first set of 8 bit data inputs of an 8 bit comparator 1140. The second set of data inputs of the 8 bit data comparator 1140 are connected to the output of buffer amplifiers 1108 of user input controls 904. The 8 bit data comparator 1140 produces a low logic level output when the two eight bit data inputs are equal, and a high logic level output if the two eight bit data inputs are not equal. In one embodiment, the data comparator 1140 is a 74HC688 integrated circuit, or equivalent.

The output of the 8 bit data comparator 1140 is communicated to additional logic 1150 to provide electrical drive capability for the duty cycle command. Thus the output of logic 1150, the duty cycle, is a high logic output when the data outputs of the second 8 bit counter 1130 equal the output from user input buffer amplifiers 1108, which represent the duty factor command. The output of logic 1150 will remain a high logic level until the output of 8 bit counter 1130 changes as a result of the ripple-carry output of the first 8 bit counter 1120 clocking the second 8 bit counter 1130. The ripple-carry output of the first 8 bit counter 1120 will only clock the 8 bit counter 1130 after a selected number of clock cycles, representing a desired duration have occurred. In this manner the output of logic 1150 is a low logic level for the amount of time represented by switch 1104 settings, at a repetition rate as selected by switch 1102 settings.

Figure 12E:
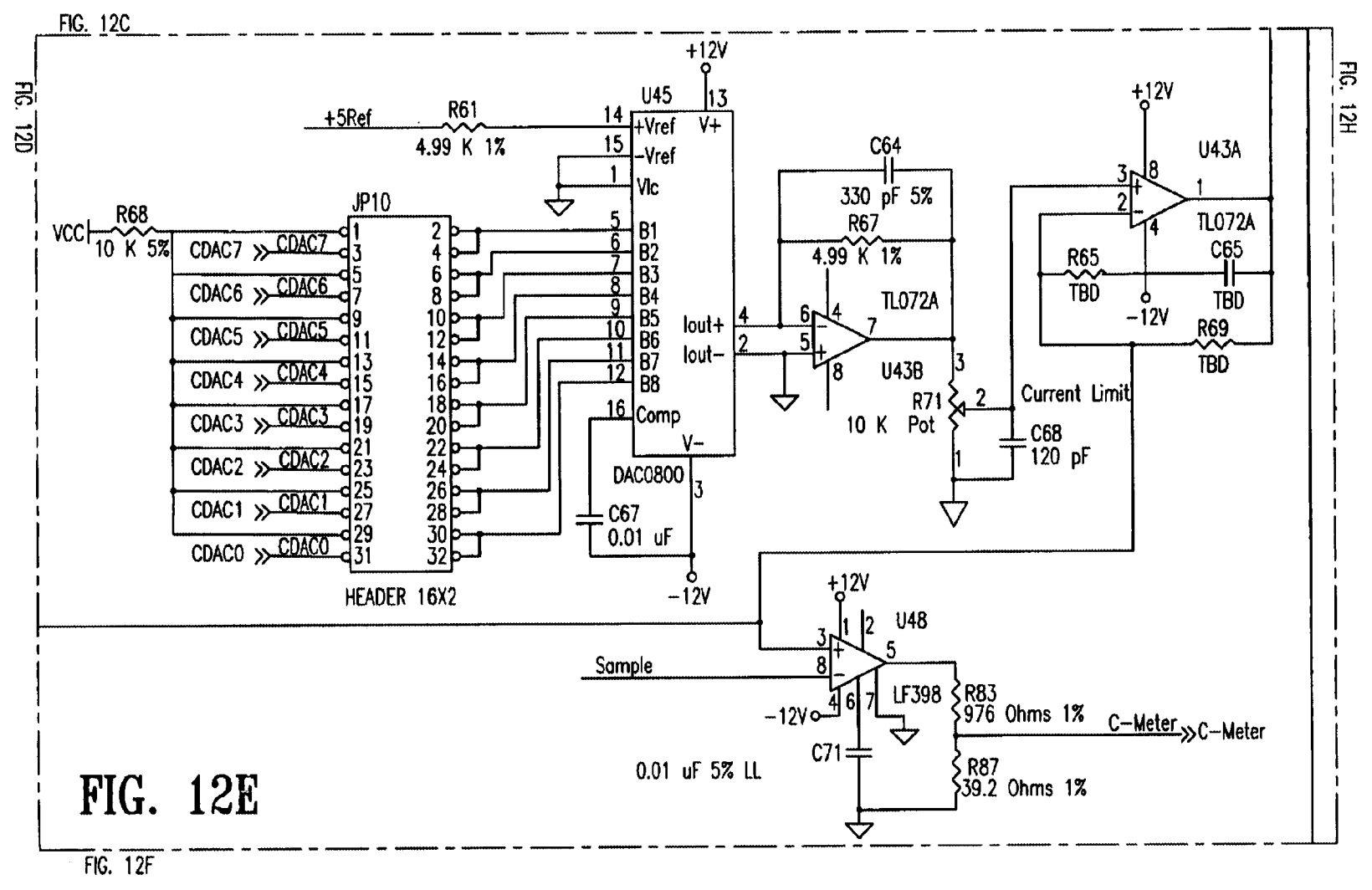

FIG. 12 is a block diagram showing additional detail of portions of signal conditioning and error amplifier 1020. In one embodiment, signal conditioning and error amplifier 1020 includes a voltage sense amplifier 1202 and a current sense amplifier 1204. Voltage sense amplifier 1202 and current sense amplifier 1204 receive signals representing the voltage and current, delivered by the electrosurgical power generator to an electrosurgical tool, respectively. The voltage sense amplifier 1202 and the current sense amplifier 1204 are configured to produce a zero to 5 VDC output representing zero to maximum voltage and current respectively.

Signal conditioning and error amplifier 1020 also includes a duty control amplifier 1206. Duty control amplifier 1206 includes a digital to analog converter configured to output a voltage representing a desired output of the electrosurgical power generator as commanded by the user.

The output of the voltage sense amplifier 1202, the current sense amplifier 1204 and the duty control amplifier 1206 are combined at gain control amplifier 1210. Thus, gain control amplifier 1210 produces a gain control signal used to control the voltage controlled amplifier 1006 so as to produce the desired output from the electrosurgical power generator. The output of the generator is then controlled to provide a desired output level, with a maximum current limit established by a programmed current limit setpoint.

The gain control signal turns the voltage controller amplifier 1006 on and off in response to user inputs for gating and duty factor control. The voltage controlled amplifier 1006 is turned off when the gain control signal is at zero voltage. In addition, when the voltage controlled amplifier 1006 is turned on, i.e. the gain control voltage is non-zero, gain control signal will control the gain of voltage controlled amplifier 1002 in such a manner as to produce the desired output of the electrosurgical power generator as reflected by the voltage sense and current sense inputs to voltage sense amplifier 1202 and current sense amplifier 1204 respectively.

Figure 13:
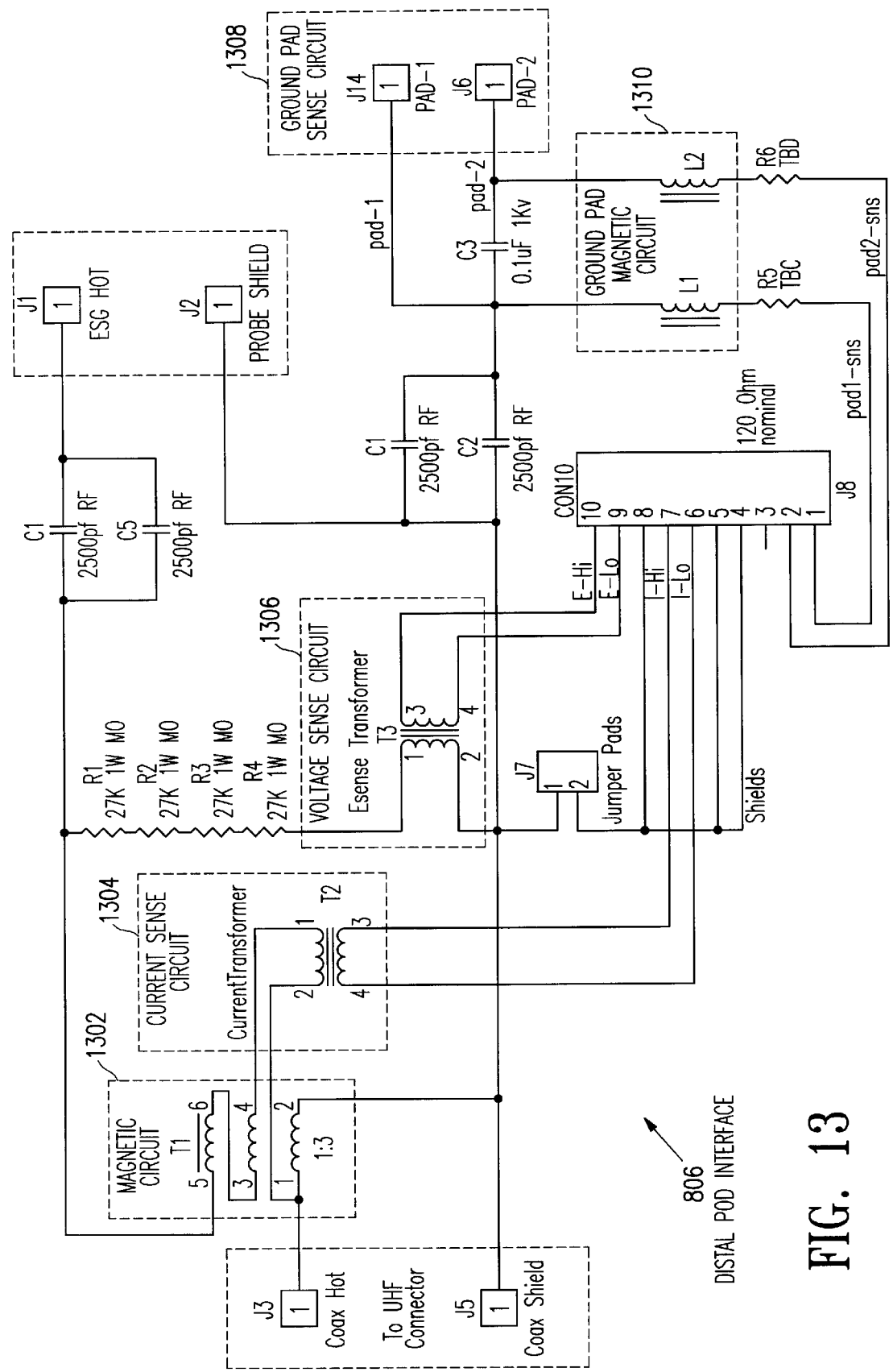
FIG. 13 is a block diagram of an embodiment of a distal interface pod.

FIG. 13 is a block diagram of an embodiment of a distal interface pod 806. In one embodiment, the distal interface pod 806 includes a magnetic circuit 1302. The magnetic circuit 1302 is configured to receive RF power from the electrosurgical power generator 802. The magnetic circuit 1302 provides an impedance matching network, so as to provide a desired load for the electrosurgical power generator 802. In one embodiment, the magnetic circuit 1302 provides a nominal impedance of 450 Ohms when driven with a 50 Ohm source. In other embodiments different source and output impedances are possible. In addition, the transformer show in FIG. 13 is a non-isolating transformer. In another embodiment a conventional transformer with separate primary and secondary may be used.

The distal interface pod 806 may also include a current sense circuit 1304 and a voltage sense circuit 1306. The current sense circuit 1304 and the voltage sense circuit 1306 monitor the current and voltage that are sent to the electrosurgical tool 810 and telemetry this data back to the feedback circuit 908 in the electrosurgical power generator 802. In one embodiment, the telemetry data are two voltage levels corresponding to current and voltage respectively. For example, the data corresponding to current may be a DC voltage scaled such that 0 to 1 VDC corresponds to 0 to 1 Amp. Data corresponding to voltage may be a DC voltage scaled such that 0 to 1 VDC corresponds to 0 to 120 Volts rms. In another embodiment the telemetry data are two current levels corresponding to current and voltage respectively. For example, the data corresponding to current may be a DC current scaled such that 0 to 20 mAmp corresponds to 0 to 5 Amps. Data corresponding to voltage may be a DC current scaled such that 0 to 20 mAmp corresponds to 0 to 1000 Volts rms. In another embodiment, 0 to 5 volts corresponds to 0 to 1000 Volts rms and 0 to 5 volts corresponds to 0 to 5 Amps The distal interface pod may also include a ground pad sense 1308 and ground pad magnetic circuit 1310. The ground pad sense circuit 1308 monitors the presence of the ground pad to ensure there is electrical conductivity between the patient 804 and the ground pad 814. The ground pad magnetic circuit 1310.

Figure 14:
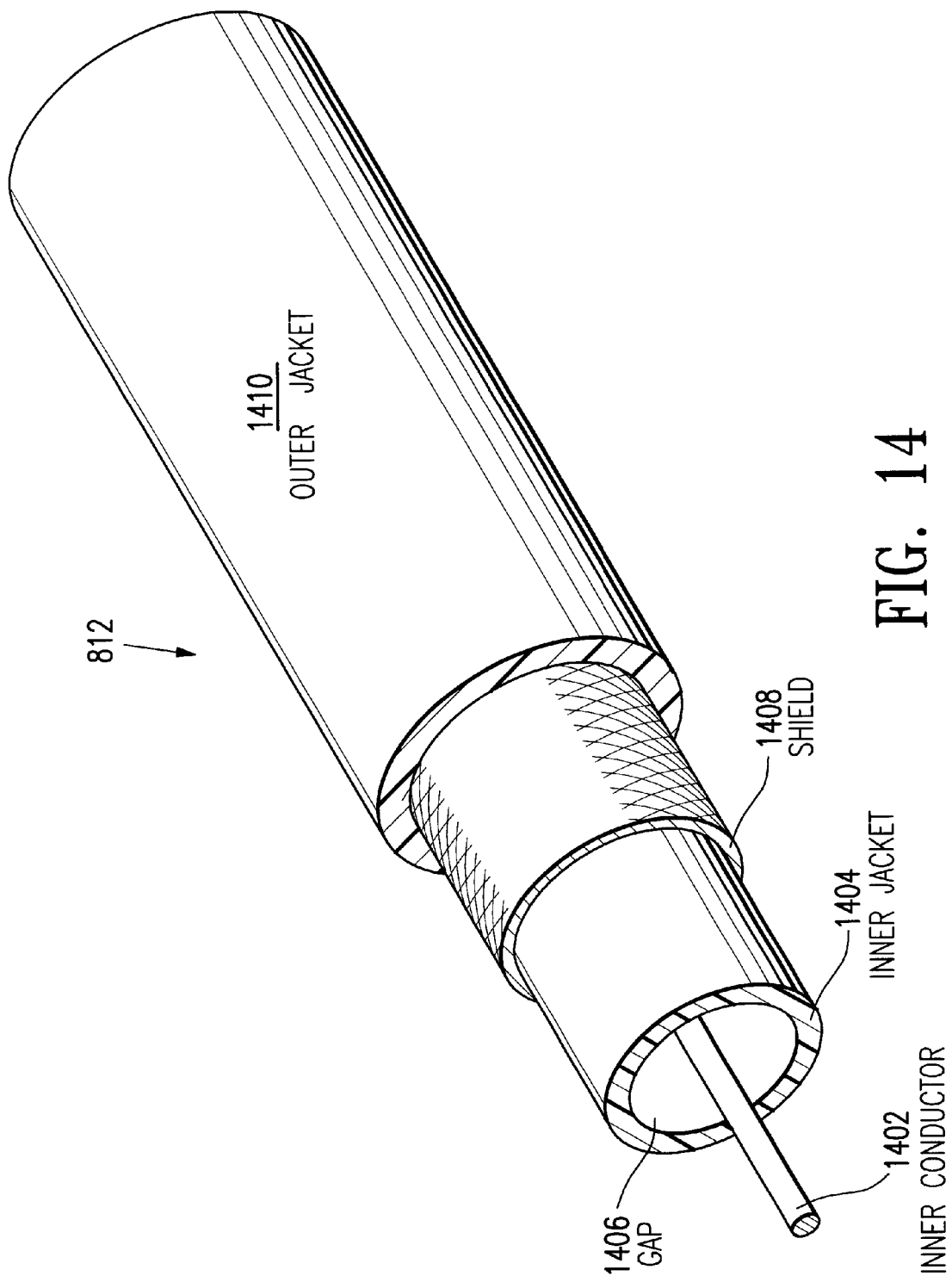
FIG. 14 is an illustration an embodiment of a flexible shielded cable.

FIG. 14 is an illustration of an embodiment of a flexible shielded cable 812. The cable 812 is designed to carry up to 5 amps at up to about 14 MHz. The cable 812 includes an inner conductor 1402. In one embodiment the inner conductor 1402 is 26 AWG solid copper magnet wire. In other embodiments, it is envisioned that other wire gauges, or stranded wire will be used, such as, for example, 27 AWG, or 25 AWG. In another embodiment inner conductor 1402 may be plated with silver or gold due to skin effect of RF signals as they propagate in conductors. Completely surrounding the inner conductor 1402 is an inner jacket 1404. In one embodiment, the inner jacket 1404 is made of a flexible material such as silicone. In another embodiment, the inner jacket 1404 may be made from HF material, such as, polypropylene. Between the inner jacket 1404 and inner conductor 1402 is a gap 1406. In one embodiment, the gap 1406 is filled with air. In other embodiments, the gap 1406 may be filled with foamed material, or solid material.

Surrounding the inner jacket 1404 is an electrical shield 1408. The shield is typically grounded and reduces exposure of the person operating the electrosurgical tool 810, as well as the patient 804, to RF radiation. In one embodiment, the shield is made from an electrically conductive braid, or spiral wrap, providing a minimum coverage of 90%. In another embodiment the shield is made from an electrically conductive foil. In other embodiments the shield may be a conductive fiber overwrap, conductive coating of the center insulator or conductive coating of the inner surface of the outer jacket with a drain wire.

Covering the shield 1408 is an outer jacket 1410. The outer jacket 1410 protects the internal portions of the cable 812. In one embodiment, the outer jacket 1410 is made from silicone. In one embodiment, the cable 812 is terminated at one end in a BNC connector, such as, for example, an AMP Economy Series P/N 414650 or equivalent.

The above described construction of the cable 812 minimizes exposure of individuals in the area near the cable to RF radiation while still maintaining flexibility to minimize interference with a surgeon's operation of the electrosurgical tool 810. Flexibility is improved by the ability of the cross section to distort in shape when bent. The airgap reduces capacitance due to airs low dielectric constant.

There are two distinct phases in electrosurgical cutting: a starting phase; and a sustaining phase. When an inactive electrode of an electrosurgical cutting tool is placed against tissue there is conductive coupling between the electrode and the tissue. Typically, the conductive coupling between the inactive electrode and the tissue presents the lowest impedance load to the electrosurgical power generator during an electrosurgical procedure. When the electrosurgical power generator is activated it imposes a voltage, typically a voltage in the radio frequency (RF) portion of the electromagnetic spectrum, on the electrode. The voltage imposed on the electrode causes current to flow through the tissue adjacent to the electrode. The current flowing through the tissue heats the tissue. The highest current density, and therefore the most heating, is in the tissue closest to the electrode.

As the temperature of the tissue rises, the tissue begins to it desiccate. During desiccation a steam layer will form between the electrode and the tissue, increasing the impedance presented to the electrosurgical power generator. If an adequate voltage is present on the electrode, the steam layer will begin conducting current. Current flows from the electrode through the steam layer and into the adjacent tissue. The current flow continues the process of desiccation of the tissue, and thereby continues the cutting of the tissue. With the onset of the steam layer, the desiccation and cutting continue, and the electrosurgical process enters the sustaining phase.

During the sustaining phase, cutting will continue as long as an adequate RF voltage is present at the electrode. Reducing the RF voltage on the electrode will end the sustaining phase, causing the cutting of the tissue to stop. Cessation of cutting may result in the deposition of carbon and biologic material on the electrode. This may result in re-establishment of proper cutting conditions more difficult. Increasing the RF voltage above the level required to maintain the sustaining phase results in excessive power dissipation in the tissue and may lead to an increase in collateral tissue damage.

The proper RF voltage for an electrosurgical procedure depends, in part, on the type of tissue encountered during the procedure. For example, experimentation has shown that typical muscular or glandular tissue presents a nominal 200 to 300 ohm load to an electrosurgical power generator that is connected to a typical electrosurgical scalpel blade or loop electrode. A typical electrosurgical scalpel may have a blade with a cross section of 0.020 inches. During the surgical procedure approximately 0.150 inches of the blade's length is typically in contact with tissue. Thus approximately 0.003 square inches of the electrosurgical blade are in contact with tissue. Test results indicate that approximately 122 volts rms is required to begin, and sustain, a cut in muscular or glandular tissue. The energy delivered into tissue with an impedance of 300 ohms, at 122 volts rms, is approximately 50 watts ($P=E^2/R=(122)^2/300$) and a corresponding energy density of 16,666 watts/square inch (50 watts/0.003 square inches). In contrast to muscular or glandular tissue, fat presents a nominal 450 to 800 ohm load to an electrosurgical power generator connected to a typical electrosurgical scalpel or loop electrode as discussed above.

New electrosurgical tools may employ longer lengths of wire for cutting, such as those disclosed in the concurrently filed applications of the present assignee entitled "BIOPSY ANCHOR DEVICE WITH CUTTER" by Quick et. al., and "SHAPEABLE ELECTROSURGICAL SCALPEL" by Burbank et. al., both filed Dec. 28, 2000 and both of which are incorporated herein in their entirety.

For example, a new electrosurgical tool may employ a length of wire for cutting with a length of approximately 1.8 inches, and a cross section of 0.010 inches. Thus, 0.018 square inches of the cutting wire may contact tissue when using the electrosurgical tool. In order to achieve the same energy density as produced by a conventional electrosurgical tool, 16,666 watts/square inch, requires approximately 300 watts (16,666*0.018). To generate 300 watts into an 800 ohm load requires the electrosurgical power generator to output nearly 490 volts rms (E=sqrt(PR)=sqrt(300*800)). Typical electrosurgical power generators presently available can only generate approximately 70 to 150 watts into an 800 ohm load.

The waveform of the output of an electrosurgical power generator may effect the amount of energy transferred to the tissue, and thereby the efficiency of cutting, during an electrosurgical procedure. Conventional electrosurgical power generators typical output a waveform which approximates a squarewave, or a complex waveform. These waveforms are typically harmonically rich and generally have a high crest factor, or ratio of peak voltage to RMS voltage. In addition, conventional electrosurgical power generators generally produce output waveforms with fundamental frequencies in the range of 300 kHz to 1 MHz and power levels of 100 to 300 watts.

It has been observed during experimentation that cutting of tissue is more effective using waveforms with higher frequencies, such as, for example, about 1 MHz to about 14 MHz, particularly about 3 MHz to about 8 MHz. Conventional electrosurgical power generators generally do not have sufficient harmonic energy present, at these higher frequencies, to effectively cut certain types of tissue, such as, for example, fatty tissue. In addition, energy present at lower frequencies, that does not effectively contribute to the cutting process, may be converted into heat and lead to damage of collateral tissue.

Problems associated with cutting fat tissue are exacerbated if a larger electrode is used, such as the electrodes disclosed in copending applications discussed above having about 0.010 to about 0.020 square inches of contact area. In order to delivery enough high frequency electrical energy to the tissue, for cutting fat tissue, particularly when cutting with a large electrode, requires a electrosurgical power generator output waveform with sufficient high frequency energy. In addition, to reduce the risk of potential damage to collateral tissue, lower frequency energy that does not effectively cut tissue needs to be minimized.

In one electrical power generator embodying features of the invention, the output waveform is essentially a sinusoidal waveform. As used herein, reference to an essentially sinusoidal waveform is a waveform with less than about 5% total harmonic distortion (THD). A sinusoidal waveform at a high frequency, for example between about 1 MHz and about 14 MHz, and at a power level up to 1,000 watts has an advantage of delivering electrical energy at a frequency most effective for cutting across a wide variety of tissue types, while minimizing the amount of energy delivered that is not effective in cutting, but rather leads to damage of collateral tissue.

The foregoing description details certain embodiments of the invention so that an understanding of the present invention can be conveyed. It will be appreciated, however, that no matter how detailed the foregoing appears, the invention may be embodied in other specific forms without departing from its spirit or essential characteristics. Moreover, those skilled in the art will recognize that features shown in one embodiment may be utilized in other embodiments. The described embodiments are to be considered in all respects only as illustrative and not restrictive and the scope of the invention is, therefore, indicated by the appended claims rather than by the foregoing description.

What is claimed is:

1. A high frequency electrosurgical generator comprising:
a control unit configured to generate a control signal;
at least one voltage controlled electrical power generating unit configured to produce a high frequency current having an essentially sinusoidal waveform having a total harmonic distortion of less than 5%.

2. A high frequency electrosurgical generator as defined in claim 1, wherein the control unit further comprises:
a set of user inputs configured to receive selection inputs desired by a user and output a user command signal;
a feedback circuit in communication with the user inputs and a distal interface pod, and configured to accept the user command signals and at least one sense circuit signals from the distal interface pod, and to output a feedback control signal in response to user command sense circuit signals; and
a signal generator in communication with the user inputs and the feedback circuit, and configured to accept the user command and feedback control signals, and to output a control signal in response to the user command and feedback control signals, wherein the control signal is a low power representation of the desired output of the power generator.

3. A high frequency electrosurgical generator as defined in claim 2, wherein the at least one sense circuit signal comprises a signal sensing the current delivered by the electrosurgical tool to the patient.

4. A high frequency electrosurgical generator as defined in claim 2, wherein the at least one sense circuit signal comprises a signal sensing the voltage delivered by the electrosurgical tool to the patient.

5. A high frequency electrosurgical generator as defined in claim 2, wherein the signal generator further comprises:

an oscillator configured to output a periodic waveform;

a low pass filter connected to the output of the oscillator, configured to receive the periodic waveform and to output essentially a sinusoidal waveform at the same frequency as the periodic waveform;

a voltage controlled amplifier connected to the output of the low pass filter and in communication with the feedback circuit, configured to receive the sinusoidal waveform and output an amplified sinusoidal waveform, wherein the sinusoidal waveform amplitude is varied in response to the feedback control signal;

a filter connected to the output of the voltage controlled amplifier, configured to receive the amplified sinusoidal waveform and output a filtered amplified waveform wherein any harmonics are attenuated;

a safety switch connected to the output of the filter and in communication with the user controls, configured to pass or block the filtered amplified waveform in response to an output received from user controls; and a buffer connector to the output of the safety switch, configured to accept the filtered amplified waveform passed by the safety switch and to output a control signal.

6. A high frequency electrosurgical generator as defined in claim 5, wherein the periodic waveform is a sine wave.

7. A high frequency electrosurgical generator as defined in claim 5, wherein the periodic waveform is a square wave.

8. A high frequency electrosurgical generator as defined in claim 1, further comprising a remote switch in communication with the control unit, configured to turn the output of the power generator on and off.

9. A high frequency electrosurgical generator as defined in claim 1, wherein the control signal is a sinusoidal waveform having a frequency of between about 1 MHz to about 14 MHz.

10. A high frequency electrosurgical generator as defined in claim 1, wherein the control signal is a sinusoidal waveform having a frequency of about 3 MHz to about 8 MHz.

11. A high frequency electrosurgical generator as defined in claim 1, wherein the control signal is a sinusoidal waveform having a frequency of about 3.4 MHz to about 5 MHz.

12. A high frequency electrosurgical generator as defined in claim 1, wherein the waveform for use with an electrosurgical tool is a sinusoidal waveform having a frequency of between about 1 MHz to about 10 MHz.

13. A high frequency electrosurgical generator as defined in claim 1, wherein the waveform for use with an electrosurgical tool is a sinusoidal waveform having a frequency of about 3 MHz to about 8 MHz.

14. A high frequency electrosurgical generator as defined in claim 1, wherein the waveform for use with an electrosurgical tool is a sinusoidal waveform having a frequency of about 3.4 MHz to about 5 MHz.

15. A high frequency electrosurgical generator as defined in claim 1, wherein the waveform for use with an electrosurgical tool provides up to about 1,000 watts of power.

16. A high frequency electrosurgical generator as defined in claim 1, wherein the waveform for use with an electrosurgical tool has a voltage of up to about 700 volts rms.

17. A high frequency electrosurgical generator as defined in claim 1, wherein the waveform for use with an electrosurgical tool has a current of up to about 5 amps.

18. A high frequency electrosurgical generator comprising:

a control unit configured to generate a control signal;

at least one voltage controlled electrical power generating unit configured to produce a high frequency current having an essentially sinusoidal waveform having a total harmonic distortion of less than 5%;

a splitter, in communication with the control circuit and configured to produce a plurality of duplicates of the control signal;

a power amplifier in communication with each of the duplicates of said plurality of duplicates of the control signal, the power amplifiers being configured to produce a high-powered output signal in response to the control signal; and a power combiner connected to each of the high-powered output signals of the power amplifiers and configured to sum the plurality of high-powered output signals effective to produce a single high-powered output.

19. A high frequency electrosurgical generator as defined in claim 18, wherein the plurality of duplicates of the control signal are four duplicates.

20. A high frequency electrosurgical generator as defined in claim 19, wherein there are four power amplifiers, each of said power amplifiers being connected to one of the four duplicates of the control signal, said duplicates of the control signal being each connected to a single one of said power amplifiers.

* * * * *